United States Patent [19]

Tegrarian et al.

[11] Patent Number: 4,613,327
[45] Date of Patent: Sep. 23, 1986

[54] APPARATUS FOR INFUSING BLOOD AND OTHER RELATED FLUIDS INTO A PATIENT'S BODY

[76] Inventors: Haig V. Tegrarian, 17 Kitchner Ct.; Mikael Ciftan, 2606 Tryon Rd., both of Durham, N.C. 27705

[21] Appl. No.: 774,381

[22] Filed: Sep. 10, 1985

Related U.S. Application Data

[63] Continuation-in-part of Ser. No. 574,199, Jan. 26, 1984, abandoned, which is a continuation of Ser. No. 240,897, Mar. 3, 1981, abandoned.

[51] Int. Cl.$^4$ ............................................. A61M 37/00
[52] U.S. Cl. ............................ 604/141; 128/DIG. 12
[58] Field of Search ...................... 222/63, 95, 334, 61, 222/103; 128/214 E, 214 F, DIG. 12, DIG. 13; 604/65, 67, 50, 154, 245, 118, 121, 140, 27, 141–150; 477/415

[56] References Cited

U.S. PATENT DOCUMENTS

| 1,661,433 | 3/1928 | Little, Jr. ........................ 417/415 |
| 3,625,401 | 12/1971 | Terry ........................ 128/DIG. 12 |
| 3,640,277 | 2/1972 | Adelberg ........................ 222/61 |
| 3,923,060 | 12/1975 | Elinwood, Jr. ............ 128/DIG. 13 |
| 4,033,479 | 7/1977 | Jacob ........................ 222/61 |
| 4,187,847 | 2/1980 | Loeser ........................ 128/214 F |
| 4,205,676 | 6/1980 | Humphrey ........................ 604/140 |
| 4,207,871 | 6/1980 | Jenkins ........................ 128/214 E |
| 4,302,185 | 11/1981 | Hall ........................ 222/95 |
| 4,308,866 | 1/1982 | Jelliffe et al. ........................ 604/67 |
| 4,430,078 | 2/1984 | Sprague ........................ 604/141 |

FOREIGN PATENT DOCUMENTS 2042091 9/1980 United Kingdom ................ 604/141

Primary Examiner—C. Fred Rosenbaum
Assistant Examiner—J. L. Kruter
Attorney, Agent, or Firm—Shlesinger, Arkwright, Garvey & Fado

[57] ABSTRACT

This disclosure describes a fully automatic, compact and portable operational device for repetitious intravenous (parenteral) infusion of fluids such as blood or blood derivatives, plasma, platelets, serum, dextrose, Ringer's solution and saline contained in pliant bags, at flow rates that not only are normally encountered but also at massive flow rates that are rather often called for but for which no such automatic device has existed. This is accomplished in a manner that frees the operator completely from attending to the device except for changing over to additional fluid bags for successive administration of fluids in such pliant bags and without loss of time. The fast response of the device is due to the special design that insures fast response both in the pressure application and retraction parts of the cycle. The device produces automatically any desired constant pressure over a wide range of pressures onto the pliant bags, over the whole compression phase of the pressure cycle. The pressure is maintained at that constant value both in time and over the entire surface of the pliant bags of various sizes.

13 Claims, 15 Drawing Figures

FOR BOLT TO ATTACH TO BACK PLATE 68

FOR SCREWS TO ATTACH TO CLAMP 45

APPARATUS FOR INFUSING BLOOD AND OTHER RELATED FLUIDS INTO A PATIENT'S BODY

This application is a continuation-in-part, of application Ser. No. 574,199, filed Jan. 26, 1984, now agandoned, which is a continuation of application Ser. No. 240,897, filed Mar. 3, 1981, now abandoned.

BACKGROUND OF THE INVENTION

1. Field of the Invention

This invention is a device that automatically provides and maintains any desired amount of pressure within a wide range of pressures over pliant fluid bags with tubular flow outlets thereby providing a simplified effective means of parenteral fluid infusion into patients with minimal supervision on the part of the operator of the device.

2. Background of the Invention

Parenteral infusion of fluids into patients comprises a major subsidiary component of the operational procedures involving the patient not only during surgery but before it in many emergency procedures, and post operatively during recovery periods and thereafter. It is also common knowledge that almost all individuals who have experienced on themselves even the simplest gravity type infusion outside the operating room, have experienced the often dangerous and at least annoying situation, namely the need to beckon the nurse frequently to tend to the infusion device to assure the desired constant flow.

Because the same problem becomes much more acute in the operating room due to the critical dependence of the vitality of the patient on a variety of fluids—such as blood, serum, dextrose—and medications introduced into the patient via such fluids, the problem in this particular operational condition has been attacked by ingenious means described in detail in the following subsection.

The original historical constraint of being forced to infuse fluids in such geographical areas where electrical power did not or could not exist, plus the continued use by physicians of the blood pressure measuring apparata have caused the prime mover of these devices to be limited to the human fist with which pressures in the range of 300 millimeters of mercury can be achieved. Such devices have therefore been so designed as to be dictated by the pressure that only one human fist can product on a rubber ball that fits in the first of one hand leaving the other hand free to manipulate adjustments etc. on these apparata. Even with this constraint of the marriage of the human fist to the all-familiar rubber squeeze ball, ingenious mechanisms have been proposed that use lever arms as in the disclosure of John Vaden Terry in U.S. Pat. No. 3,625,401 or turn handles as in the disclosure of Walter J. Jinotti in U.S. Pat. No. 3,565,292. Notwithstanding that these patent disclosures and several others that shall be described in the following subsection constitute significant contributions to the art, they do suffer from one or more drawbacks that shall be documeted in detail in the following subsection.

A search of prior patents for infusion devices detailed below as well as an analysis of such devices existing in actual use show the absence of completely automatic version of such an infusion device that is also compact and simple to be an operationally practical embodiment for actual use. The reason for this missing link can be traced to the absence of a reasonably thorough quantitative analysis of the interdependences of all of the parameters of such an automatic device in the framework of well established principles and concepts of physics and engineering. The quantitative analysis disclosed herewith, in the section of the detailed description of the invention, is an integral part of the present disclosure and reveals that: due to the specific design that is being disclosed the device has low air volume compression requirements and substantially high pressures can be obtained with a very low horsepower prime mover, for example, a direct current motor of very small dimensions (of the order of one and a half inch in diameter, two inches long) with very low power (fractional horsepower) sufficient for massive as well as normal infusion of fluids. It is also shown in this disclosure that the said miniature compressor can be so designed as to be operated at low RPM for massive infusion and therefore can have sufficiently low noise (sound-noise) to be acceptable for the operating room environment. Without such characteristics of compactness, portability and low noise, an infusion device would not have a wide scope of applicability even if fully automated.

3. Description of the Prior Art

Recent communications in the journals "Anesthesia and Analgesia" and "Anesthesiology" indicate that the Fenwal (registered trademark) infuser and its variants similar to that of U.S. Pat. No. 4,090,514 of Hinck et al are the most commonly used infusers. These same communications, however, point out the drawbacks of these devices. We shall first discuss these communications and then describe a number of patent disclosures on fluid infusers.

Jordan Waldman and Toomas Reband in the journal "Anesthesiology", on pages 73 and 74 of vol. 50, in January 1979 point out that "conventional hand-bulb cylinders or pressurized bags for infusing blood rapidly are unsatisfactory when rapid, constant flow infusion is desired." They refer to the Fenwal infuser which is a pliant inflatable bag to which another layer of cloth is attached in such a way as to be able to insert the fluid bag between the bag and the cloth and apply pressure on the fluid bag by use. The reason for this missing link can be traced to the absence of a reasonably thorough quantitative analysis of the interdependences of all of the parameters of such an automatic device in the framework of well established principles and concepts of physics and engineering. The quantitative analysis disclosed herewith, in the section of the detailed description of the invention, is an integral part of the present disclosure and reveals that: due to the specific design that is being disclosed the device has low air volume compression requirements and substantially high pressures can be obtained with a very low horsepower prime mover, for example, a direct current motor of very small dimensions (of the order of one and a half inch in diameter, two inches long) with very low power (fractional horsepower) sufficient for massive as well as normal infusion of fluids. It is also shown in this disclosure that the said miniature compressor can be so designed as to be operated at low RPM for massive infusion and therefore can have sufficiently low noise (sound-noise) to be acceptable for the operating room environment. Without such characteristics of compactness, portability and low noise, an infusion device would not have a wide scope of applicability even if fully automated.

3. Description of the Prior Art

Recent communications in the journals "Anesthesia and Analgesia" and "Anesthesiology" indicate that the Fenwal (registered trademark) infuser and its variants similar to that of U.S. Pat. No. 4,090,514 of Hinck et al are the most commonly used infusers. These same communications, however, point out the drawbacks of these devices. We shall first discuss these communications and then describe a number of patent disclosures on fluid infusers.

Jordan Waldman and Toomas Rebane in the journal "Anesthesiology", on pages 73 and 74 of vol. 50, in January 1979 point out that "conventional hand-bulb cylinders or pressurized bags for infusing blood rapidly are unsatisfactory when rapid, constant flow infusion is desired." They refer to the Fenwal infuser which is a pliant inflatable bag to which another layer of cloth is attached in such a way as to be able to insert the fluid bag between the bag and the cloth and apply pressure on the fluid bag by inflating the infuser bag, thus squeezing the fluid bag between the infuser bag and the said attached cloth; a variant of this is disclosed in U.S. Pat. No. 4,090,514 by Hinck et al where the secondary "cloth" is made of two pieces with Velcro (trademark) type means for locking the two pieces of the additional enveloping portion that go around the fluid bag. Waldman and Rebane suggest the use of pressurized gas, in place of air or gas from the hand squeezed hand-bulb, that is to be obtained from wall oxygen in the hospital or from pressurized gas cylinders plus a pressure-flow regulator. In answer to this suggestion, James S. Hicks suggest in "Anesthesiology", vol. 51, in October 1979, on page 364, the use of the "orthopedic tourniquet system" driven by oxygen cylinder when massive, rapid infusion of blood is necessary, with the tourniquet attached to the Fenwal pressure bag line. In addition to these suggestions, L. Brian Ready discusses in "Anesthesia and Analgesia", vol. 58, in March–April 1979, on page 155, the need for rapid intravenous infusion, "a means of maintaining a rapid infusion rate without the need for repeated manual inflation of a blood pump". He suggests the use of an "automatic tourniquet" in conjunction with the Fenwal bag, but Alan Jay Schwartz, David R. Jobes and Norig Ellison, in response to this suggestion also point out in "Anesthesia and Analgesia" in vol. 59, March 1980, on page 226, that while Ready's suggestion is a good one, they "have experienced one occasion where the bulging seam of the plastic bag containing heparin solution split, resulting in a shower of solution of the operating field, the anesthesia machine and the adjacent personnel. Fortunately, the bag was heparin, not a transfusion". There is further evidence that the same has happened with blood.

In addition to controlled pressure, a constant high pressure is needed for aiding surgery by the infusion of cardio-plegic solution during cardio-vascular/open heart operation or procedure.

Thus the need for a completely self-contained compact unit with a very carefully controlled pressure that is constant in time and over the whole fluid bag, that does not rely on high pressure gases from gas cylinders or from wall gas outlets of a hospital is established.

Study of previous inventions of pressure infusion devices, to be described below, can be summerized as variants of four principle methods of application of pressure: (1) "Bag on bag" method as that of Howard Helmut Hinck et al (U.S. Pat. No. 4,090,514) and that of Bede Stanislaus Nugent (U.S. Pat. No. 3,895,741); (2) "Rigid movable wall on bag" advanced, for example, by a screw-spring system as that of Walter J. Jinotti (U.S. Pat. No. 3,565,292) or of John Vaden Terry (U.S. Pat. No. 3,625,401); (3) "Squeeze out" type as that of Ellis Whiteside Clarke (U.S. Pat. No. 3,949,744) or variants of it such as the I.V. STAT (trademark) that incorporates a spring loading mechanism for squeezing out; (4) Related fluid dispensing methods such as that of Albert R. Uhlig (U.S. Pat. No. 4,147,278) which can be briefly described as "Air on a bag in rigid container".

The Hinck type infuser (which is a variant of the commonly used Fenwal device mentioned earlier), in addition to being first operated (and therefore not automatic), uses a Velcro fastener for the envelope that encases the fluid bag. It suffers from the same problems of uncontrolled pressure (causing bursting) as well as the Velcro fastener becoming inactive due to capture of lint etc. in the operating room environment. The Nugent version is specifically designed to prevent infusion of gas trapped in the fluid bag, by allowing the gas to rise to the upper part of the bag. The same result can be achieved with a rigid wall type infuser as well. It also has introduced an operable door concept which is useful. Otherwise, this device also has the same disadvantages as the Hinck one in so far as pressure control is concerned.

Of the rigid but moveable wall type infusers, the Jinotti device does not provide a constant pressure on the fluid bag because it uses Hooke's Law (using a spring loading), i.e. force=the spring constant times the displacement; therefore as the bag becomes depleted, and the spring extends back from where it was compressed to, the force (and therefore the pressure) on the bag changes. Even if a variant of it is designed so as to be able to readjust the force on the spring by recranking the screw, it will still require repeated intervention by the operator. Furthermore if a nonlinear spring is designed so as to provide a constant pressure, the spring will provide only a particular pressure and will not provide a wide range of variably controlled pressures for infusion of different fluids nor for infusion of any given fluid at different flow rates.

The Terry device is mechanically too complicated for practical use. It uses liquid-fluidic components interspersed with pulleys, strings and lever arms. It is intrinsically slow because it uses liquid fluidics as opposed to gas, and furthermore the fluidics used is not in the modern sense which has been recently developed to simulate electronic components such as amplifiers. Therefore, it is impractical for rapid, repetitive sequential application of the device for massive infusion.

The Clarke device is singularly disadvantageous for rapid massive infusion because it has no quantitative control on the pressure and requires constant attention by the operator. In conjunction with this device there is a variant, namely the I.V. STAT, that has been discussed above.

In many of the devices mentioned above, a spring is used in conjunction with a piston for the main purpose of providing pressure derived from the potential energy stored within the spring; we note that in the present disclosure a spring is also used but for the sole purpose of pressure-free retraction of such a piston and therefore a spring having a negligable spring constant can be used; this point is discussed further in the disclosure.

Because the present device will allow operation at pressures much higher than those used up to now, it is expected that previous designs of fluid bags such as that of Albert Frank Bujan et al (U.S. Pat. No. 3,915,212) may be modified to withstand higher pressures for much more rapid infusion for critical uses.

It is also to be expected that the presently disclosed device will open up opportunities for the development of new types of blood filters that can be used in conjunction with massive infusion applications at high pressures.

THE INVENTION

This invention is a device for the fully automatic, controlled and sustained application of pressure onto pliant bags containing fluids such as blood, dextrose, etc. consistent with the operational requirements for parenteral infusion of such fluids into patients, and in consonance with the requirements for the use of additional apparata such as filters and bloodwarmers in conjunction with this device. Furthermore, a single embodiment of this said device can deliver pressure in a wide range to ensure normal to massive fluid infusion rates. Normal infusion is generally understood to be the delivery of 500 ml. of fluid from the container into the body in 5 to 10 minutes, and massive infusion is the delivery of 500 ml. of fluid to the body in 1 minute or less.

The uncovering of the heretofore non-obvious possibility that a simple and practicable embodiment of the said device can be achieved, based on a quantitive analysis of the total system, is a pivotal component of this claimed invention.

The power of this analytic approach (detailed below) is further demonstrated by the potential improvements in internal and peripheral components that it suggests for optimal infusion.

BRIEF DESCRIPTION OF DRAWINGS

1. Brief Description of the Figures

The invention is described in detail below with reference to the following drawings.

Figure 1:
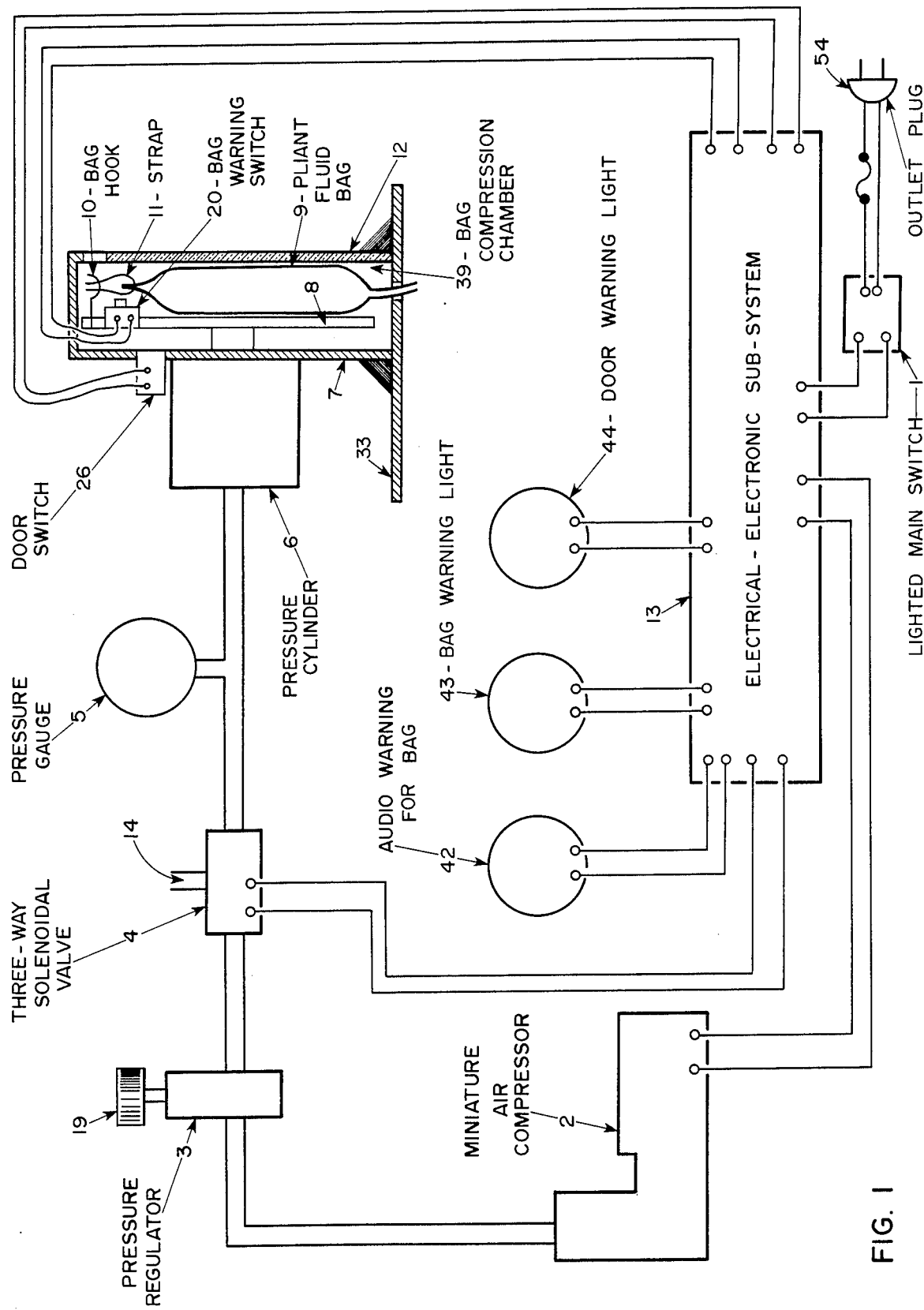
FIG. 1 is a schematic representation of the Automatic Infusion Device, of the present invention.

2. Parts of the Figures
1. Main switch, make and break, lighted when on
2. Miniature air-compressor
3. Pressure regulator
4. Three-way solenoidal air or gas valve
5. Pressure gauge
6. Pressure cylinder
7. Central vertical stationary support plate
8. Pressure push plate or "compression plate"
9. Pliant fluid bag
10. Hook for pliant fluid bag
11. Strap for pliant fluid bag and hook 10
12. Stationary vertical end wall
13. Electrical-electronic control sub-system
14. Vent port of three-way solenoidal valve 4
15. Piston head of piston in pressure cylinder 6
16. Rear cylinder wall of pressure cylinder 6
17. Pressure cylinder piston rod
18. Fluid exit port of pliant fluid bag 9
19. Control knob of pressure regulator 3
20. Bag warning switch-normally open momentary push-button type
21. U-packing seal of pressure cylinder piston head 15
22. Piston retraction spring for pressure cylinder piston 15
23. Air relief port for pressure cylinder
24. Air entrance port of solenoidal valve 4, compressor side, normally closed (closed when no current flows in coil 34 of same valve)
25. Main fuse
26. Momentary push-button normally open sub-miniature switch for door 35 of bag compression chamber 39
27. First Relay
28. Electronic latching circuit
29. Coil of Seond Relay 30
30. Second Relay
31. A.C. to D.C. converter for compressor motor 32 of miniature air-compressor 2
32. Air-compressor motor
33. Base (bottom) plate of the whole device
34. Coil of the three-way solenoidal air or gas valve
35. Door of the fluid bag compression chamber 39
36. A.C. to D.C. converter for relays and electronic latching circuit
37. Silicon controlled rectifier
38. Resistance $R_c$ to grid of the silicon controlled rectifier 39. Compression chamber for pliant fluid bag
40. Handle of the Automatic Infusion Device
41. A.C. to D.C. converter for audio and video warning signals (buzzer and light)
42. Buzzer for bag
43. Warning light for bag
44. Door warning light
45. Clamp for mounting the Automatic Infusion Device on a pole
46. Compressor shaft (of miniature air-compressor 2) at end of motor RPM reduction gear if such gear used
47. Crank arm radius
48. Translation arm of air-compressor 2
49. Piston head of miniature air-compressor 2
50. Cylinder of miniature air-compressor 2
51. Intake orifice valve on piston head 49
53. Exhaust orifice valve on cylinder 50
53. Tube connecting miniature air-compressor cylinder for pressure cylinder 6
54. Hospital grade A.C. outlet plug
55. Pressure generation-control chamber (PGCC) left of central vertical stationary plate in a frontal view
56. D.C. main switch
57. A.C.-D.C. mode selection toggle switch
58. D.C. fuse
59. D.C. plug, for example a car cigarette adaptor type
60. Capacitor for A.C. to D.C. converter for compressor motor 32
61. High power rectifier diode for A.C. to D.C. converter 31
62. Collar for piston
63. Door frame (load bearing)
64. Transparent overlay for door frame 63
65. Magnetic or other door lock
66. Door knob
67. Top plate
68. Back plate
69. Fuse for air-compressor motor
70. Bracket on plate 12 folding over top plate 67, back plate 68 and base plate 13
71. Brackets to fasten rigidly central plate 7 to base plate 13 and top plate 67
72. Opening on plate 12 for hook 10
73. Opening on plate 12 for bag nipples for medicine injection into bag
74. Plate for left hand side end closure
75. Chamber for hand bulb and/or coupling for externally pressurized gas source
76. Front panel, front plate
77. Piston head of air-compressor in the design of FIG. 11
78. Cylinder wall of air-compressor
79. Involuted or convoluted diaphragm for air-compressor
80. Collar for piston rod of air-compressor
81. Ball bushing for collar 80
82. Piston rod of air-compressor
83. Transformers for A.C. to D.C. convertors
84. A.C. to D.C. convertor for door light and solenoid of three-way air valve
85. Footings for Automatic Infusion Device
86. Collar for piston rod of pressure cylinder
87. Ball bushing for collar 86 and piston rod 17

DETAILED DESCRIPTION OF THE INVENTION

Figure 3:
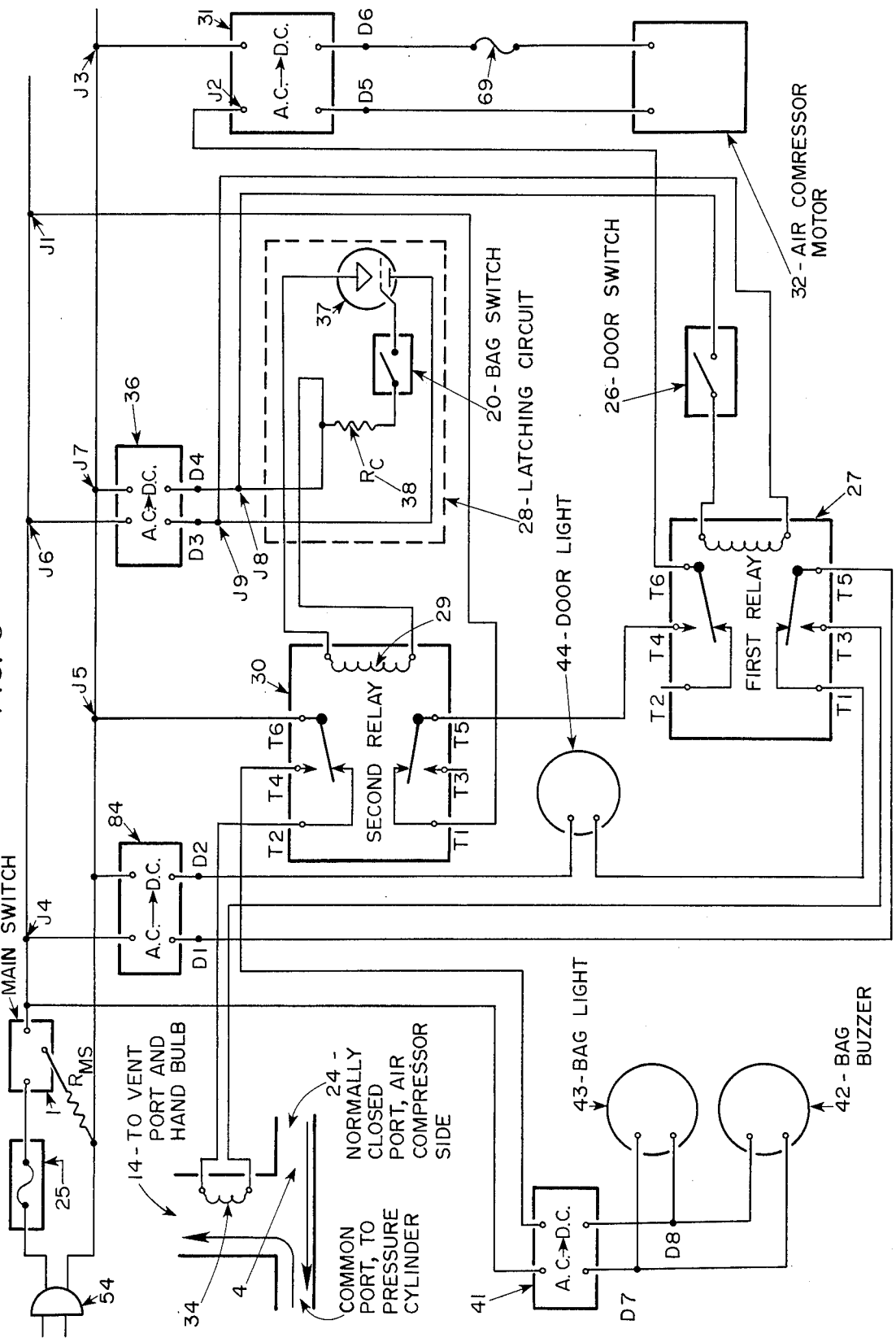
FIG. 3 is a diagram showing the entire electrical-electronic system.

FIG. 1 shows the major components of the infusion device hereby disclosed. Main switch 1 activates the air-compressor 2 which in turn delivers pressurized air to the pressure regulator 3, to the three-way solenoidal valve 4, pressure gauge 5 and finally to air-compression cylinder 6 fastened to plate 7. The pressure is transferred via a piston in cylinder 6 to a compression plate 8 that applies pressure to pliant fluid bag 9. Further details of the compression cylinder and compression chamber are shown in FIG. 4, while details of the electronic electrical subsystem are shown in FIG. 3.

Figure 4:
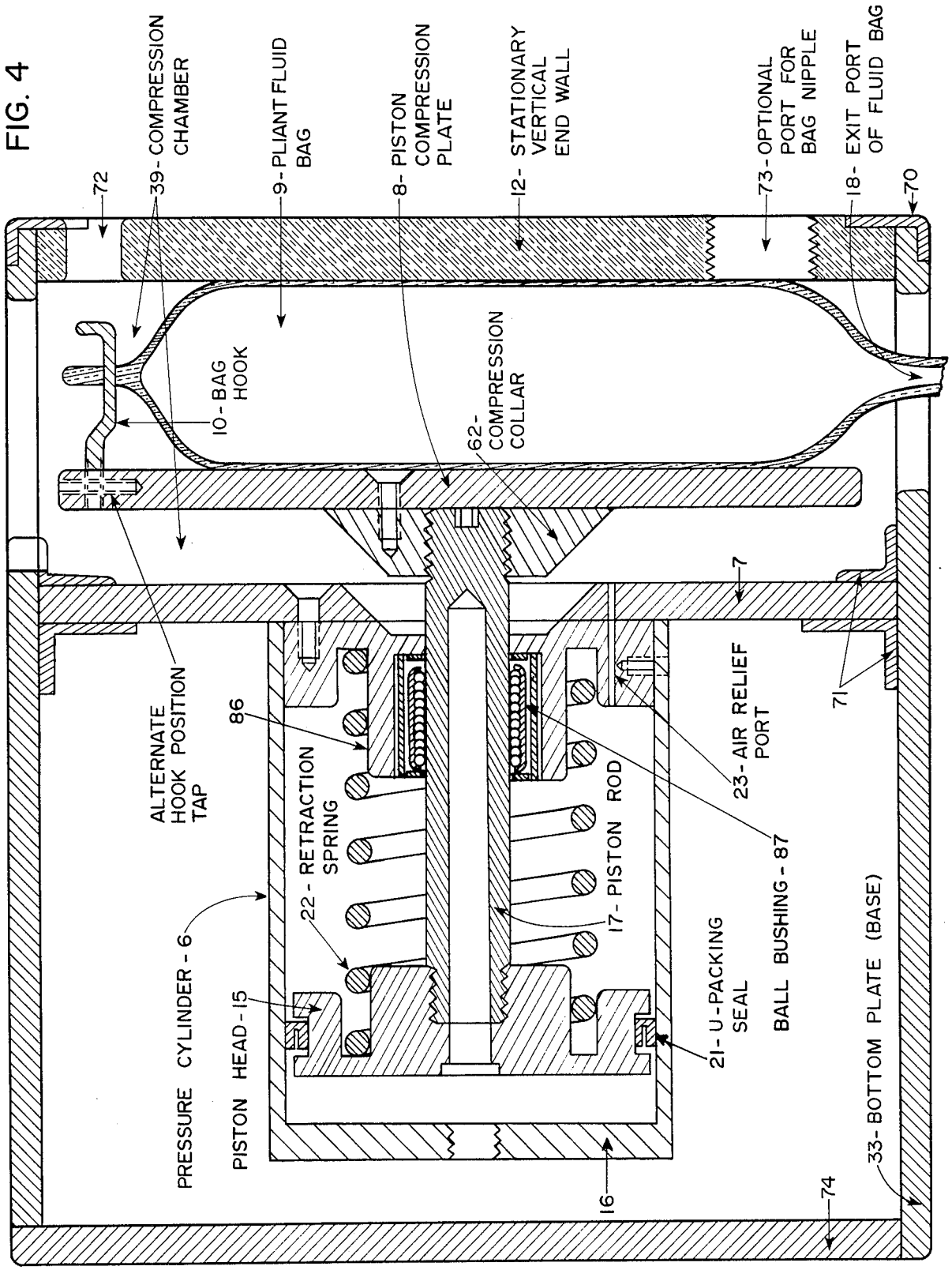
FIG. 4 is a vertical cross-sectional view of the Automatic Infusion Device shown in FIG. 2, viewed from the front, showing details of the compression cylinder and bag compression chamber.

We start with piston head 15 (see FIG. 4) in its retracted position in the pressure cylinder 6 namely, the piston head 15 adjacent to the rear cylinder wall 16 (see FIG. 1 and FIG. 4). The pliant fluid bag 9 is then hung from hook 10, using the optional strap 11 shown in FIG. 1 and FIG. 2. This hook is attached to piston pressure plate 8 and can protrude through an opening in the stationary vertical end wall 12.

Upon pressing main switch 1 which is a "make and break switch", household 110/60 A.C. activates a miniature air-compressor 2. Air is then directed under pressure to pressure regulator 3.

At the same time as when the main switch is activated the three-way solenoidal air valve 4 is activated by the electronic control unit 13 to allow the pressurized air from the pressure regulator 3 to pass through the said solenoidal valve 4 simultaneously to pressure gauge 5 and pressure cylinder 6, and the same solenoidal action on air valve 4 closes the exit air vent port 14.

The continual supply of air under pressure from the miniature air-compressor 2 insures that the piston head 15 (inside the pressure cylinder 6) is forced away from the rear cylinder wall 16 transmitting at the same time this same force via the piston rod 17. This said rod 17 passes freely through the stationary central support plate 7 (which is securely fastened to base plate 33) to the piston pressure plate 8 which is permanently attached to the said rod 17. The piston pressure plate 8 moves towards the stationary vertical end wall 12 which is securely fastened to base plate 33, applying pressure on the pliant bag 9 which resists this motion thereby starting the initial flow of fluid out of the exit port 18 of the fluid bag 9. Due to the pressure regulation action of the pressure regulator 3, a constant pressure is developed and maintained onto the pliant bag irrespective of pressure fluctuations arising from the miniature air-compressor 2. This said constant pressure is set at any desired value in a broad range by turning knob 19 of the pressure regulator 3. This same pressure is maintained up and until the complete depletion of fluid in the pliant bag 9 upon which automatic retraction of the piston pressure plate 8 is activated as follows.

A normally open momentary push-button switch 20 is mounted on the piston pressure plate 8 outside the periphery of the pliant bag 9 and in the direction of plate 12 such that when plate 8 and plate 12 come together due to the said depletion of the fluid in pliant bag 9, the said switch 20 is then closed. At this very instant two functions are simultaneously triggered. The first action is that an audible as well as a visible warning signal is given so that the operator knows that the pliant bag 9 has been depleted.

The second of the two simultaneous actions (triggered by the closing of switch 20) is the channeling of air through the exhaust port 14 of the three-way solenoidal valve 4 so that piston 15 retracts. This is accomplished by an electronic latching circuit 28 (described in detail below and sketched in FIG. 3) triggered by the closing of switch 20.

This electronic action opens the vent 14 of valve 4 and closes simultaneously the entrance port 24 (see FIG. 3) to the said valve 4. Thereupon piston spring 22 forces the piston 15 to retract towards the rear cylinder wall 16. Even though the momentary switch 20 returns to its original normally open state in this retraction process, the very latching action of the electronic latching circuit 28 insures that the solenoidal valve 4 remains in this state until and only if the main switch 1 is pushed into the break position. As an auxiliary precautionary measure a momentary push-button switch 26 is mounted on the door 35 of the bag compression chamber 39 and is circuited in such a way that the cycle will not begin or continue unless the door is in the closed position.

1. Description of the Electrical-Electronic Sub-System

The purpose of this electrical-electronic circuit is to provide a totally automatic operation of the device with minimal involvement of the operator and no loss of time in successive applications of bags of fluid for infusion. The operator simply turns on and off one switch and inserts into or removes bags from the device. The moment the fluid content of a bag is emptied two actions are triggered automatically. One action is that the piston 15 is automatically retracted so that the empty bag is free to be removed and the second action is that alarms are activated and stay on until the operator simply turns off the said switch.

FIG. 3 shows the following main components of the electronic subsystem to which the air-compressor 2 is coupled via its electrical motor 32: (a) The main fuse 25 and the main lighted switch 1; (b) the three-way solenoidal valve 4 with its induction coil 34: (c) A.C. to D.C. converter 41 for buzzer 42 and bag light 43; (d) A.C. to D.C. converter 84 for solenoidal valve 4 and door light 44; (e) A.C. to D.C. converter 36 for latching circuit 28 that includes bag switch 20, First Relay 27 in conjunction with door switch 26, and Second Relay 30; (f) A.C. to D.C. converter 31 for the D.C. electric motor 32 of air-compressor 2.

The operation of the electrical-electronic system is as follows: With an operating fuse 25, and the main switch 1 on (lighted) but subminiature door switch 26 (for pliant bag compression chamber) off (door open), First Relay 27 is off; in this state of the First Relay 27 contact T1 of said relay is connected (electrically conducting) to contact T5 of same relay, and similarly contact T2 is connected to contact T6. Independently of the door switch 26, the bag switch 20 is open or closed. First assume that the bag switch 20 is open; this causes the electronic latching circuit to be open, namely non-conducting for reasons to be described in detail below. Therefore, this said latching circuit does not allow current to flow in the coil 29 of the Second Relay 30, so that contacts T1 and T5 as well as contacts T2 and T6 of said Second Relay are connected (conducting).

Anytime the door switch 26 is open, contacts T1 and T5 of the First Relay 27 are conducting and warning light is turned on that indicates that the door is open. Furthermore, as a precautionary measure, so long as the door is open, the door switch is also open and the air-compressor can not go on because of the following reasons: the path for the current to the A.C.-D.C. converter 31 for the motor 32 is broken because starting from junction J1, current would have to pass through contacts T1 and T5 of the Second Relay but then could not pass through contacts T4 and T6 of the First Relay (since this relay is not on) to go to junction J2 of converter 31 and finally to junction J3.

Figure 2:
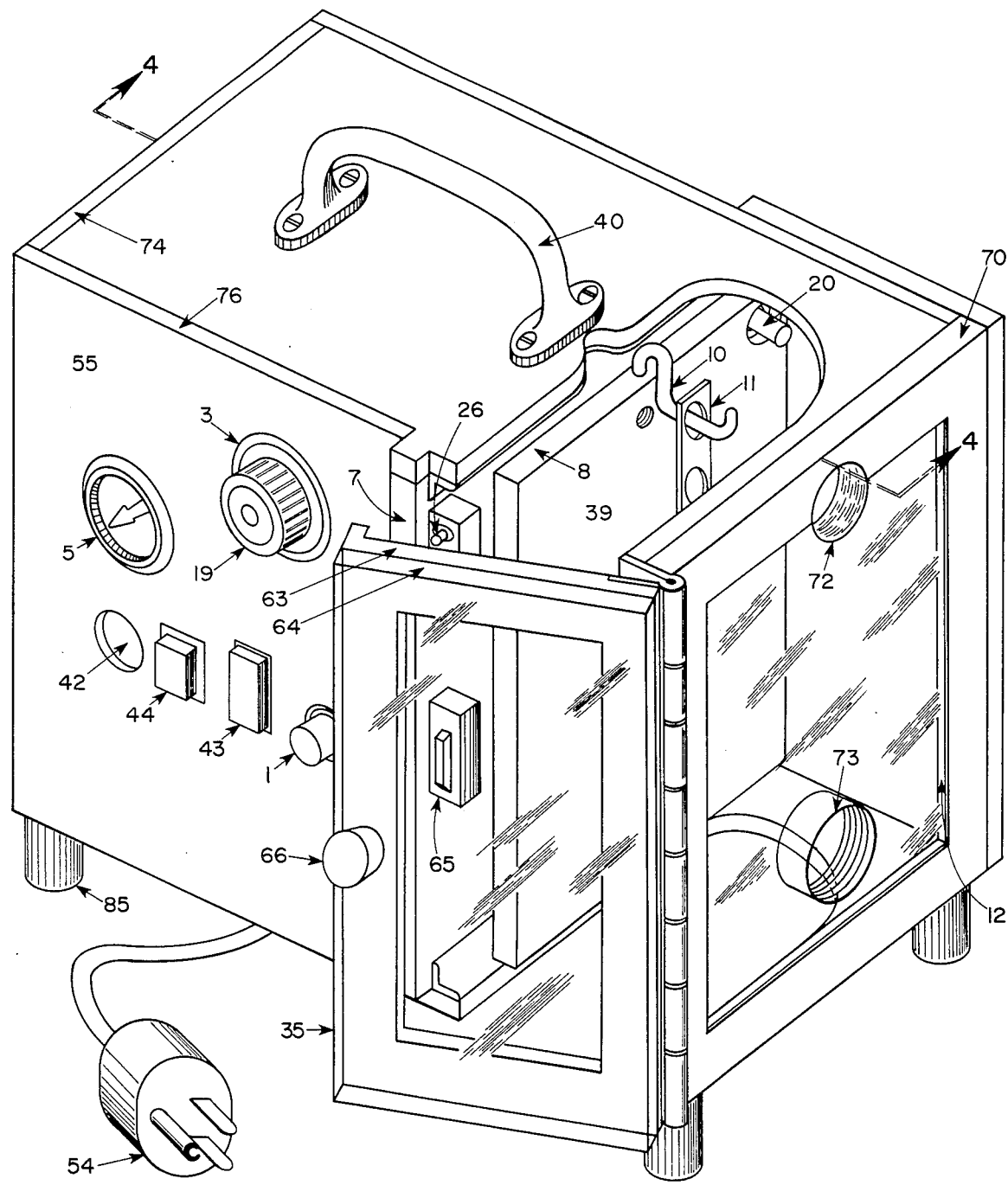
FIG. 2 shows a frontal perspective of the entire device disclosed herewith, showing also the top and right hand side of the device.

When the operator notices that the door light is on, he closes the door 35 which closes the door switch 26 attached to plate 7 apposing to the door frame 63 (see FIG. 2). While the door switch is in this closed state, the compressor motor is on because the First Relay is on and contacts T4 and T6 are now connected. Note that the bag switch 20 is still open. Concurrently, the three-way solenoidal valve 4 is activated (as soon as the door switch 26 is closed) because current can flow from junction J4 to contact T5 of the First Relay, then to contact T3 of the same First Relay, to the solenoidal coil 34, to contact T2 of the Second Relay, to contact T6 of the same Second Relay, and finally to junction J5. In this state the air valve vent 14 is closed but port 24 of same is open to the air-compressor allowing the air to pass through the said valve to the pressure cylinder 6. Now compression on the pliant bag begins and continues until all liquid is removed from the bag, at which point the bag switch 20 (see FIG. 2) closes thereby activating the latching circuit 28 (as described in the next section) while at the same time: (1) turning on both the audio and video alarms, 42 and 43, (2) turning off current in the coil 34 of the air valve 4 and releasing the compressed air in the pressure cylinder 6 through the vent port 14 so that the piston 15 retracts and pressure on the pliant bag is released.

The role of the latching circuit is that once current flows through it (when the bag switch is closed) it maintains that current flow even though the switch is re-opened when the piston retracts, and so it remains until the main switch 1 is turned off thereby cutting all current to the latching circuit, particularly through the silicon controlled rectifier 37 of the latching circuit.

2. The Latching Circuit

A.C. power from junction J6 and J7 is converted to D.C. power through the converter 36. Current from junction J8 (at the output of the converter 36) going through resistance of coil 29 of the Second Relay 30 would arrive at the cathode of the silicon controlled rectifier (SCR) 37; but when bag switch 20 is open, the resistance of the SCR is too high for current to break through so that the current that would pass through coil 29 of the Second Relay to the anode does not pass to the said anode to go to junction J9 (at the output end of converter 36). However, when the bag switch 20 is closed, a small current flows through the $R_c$ resistance 38 to the grid of the SCR 37. This current activates the SCR 37, as usual, and thus current can pass to the anode side of the SCR 37 and therefore to junction J9. Thereafter even when the switch 20 is opened, the current is maintained across the SCR 37 in the usual manner known for transistors. This current flow is broken, however, when the operator pushes main switch 1 thereby cutting off all power to the latching circuit 28.

A small but significant detail, namely the use of a push-button type single pole-single throw main switch (lighted when "on") in conjunction with a latching circuit designed to have just long enough decay-time constant adds two additional desirable quantities to the Automatic Infusion Device: (1) if the push-button is pushed again immediately after it has been pushed once for retraction to take place, then the device ignores this repeated command so that the device can continue to complete retraction and will not change over to the pressure application mode—this is very desirable so as to avoid accidental compression and adds an additional safety measure particularly in conjunction with the door switch and door warning controls (2) the operator does not have to pay close attention to the panel of the Automatic Infusion Device to see which position of the switch is for "on" and which is for "off"—he simply presses a button.

Thus all the actions of the operator are reduced to pressing a button and changing bags.

3. The Miniature Air-Compressor

Figure 8:
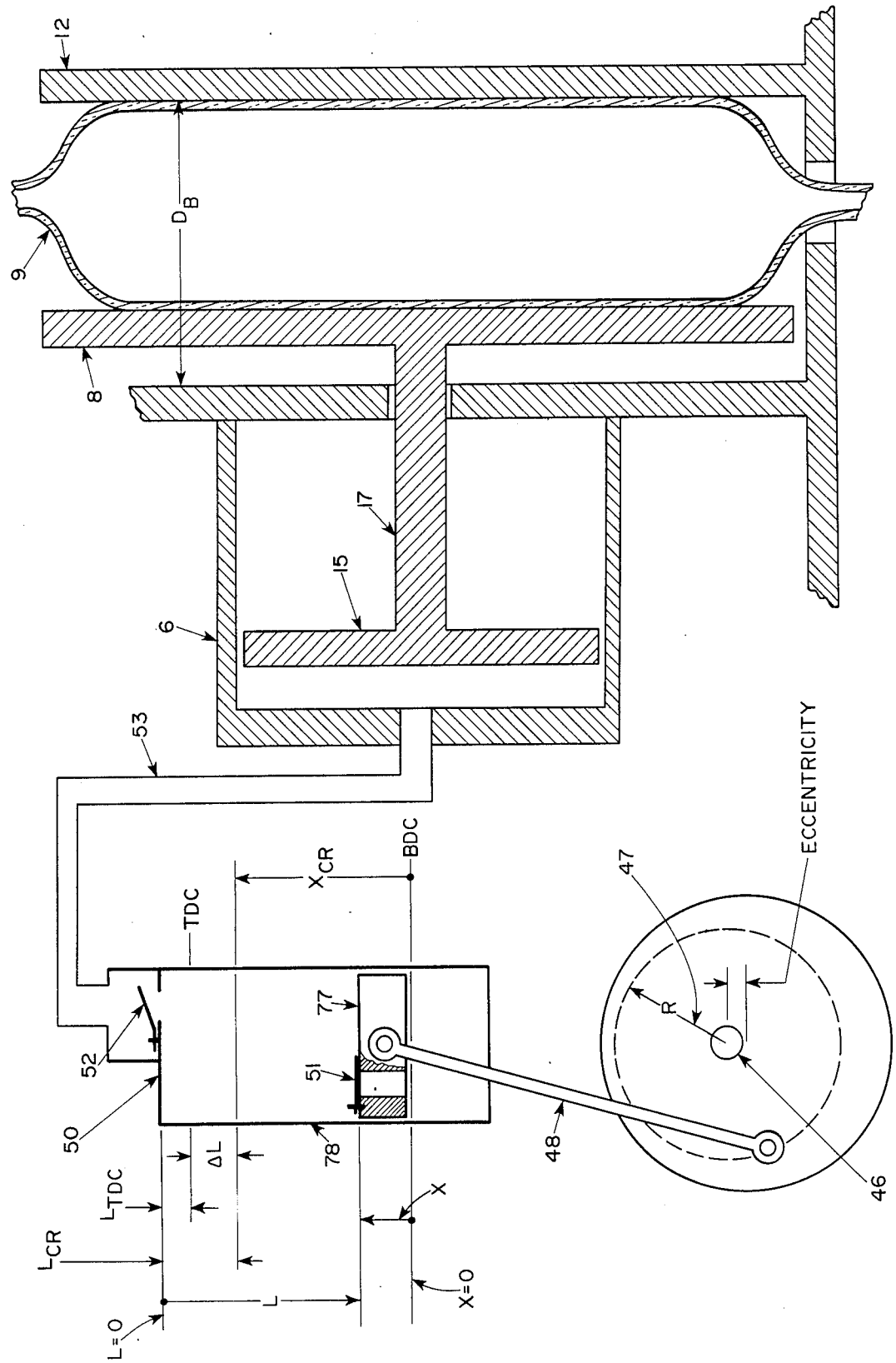
FIG. 8 is a schematic of the main air-compressor and bag compression components that are used in quantitative analysis of the device in subsection 3 of the detailed description of the invention.

FIG. 8 depicts a schematic diagram of the essential components and the parameters for a quantitative analysis of a "compressor-pressure cylinder-bag compression chamber" system for fluid infusion. In order to make the hereby disclosed Automatic Infusion Device practical for operating room, emergency, recovery, hospital ward operations and for applications in ambulances, it has to be compact (sufficiently small in size), have an acceptable weight and be whisper quiet. The analysis presented herein shows that the horsepower (HP), the revolutions per minute (RPM) of the electrical motor that drives the piston of a reciprocating type air-compressor and the RPM of the compressor flywheel (which determines in part the noise level of the air-compressor) are the most important parameters.

Referring, in part, to quantities shown in FIG. 8, we define the following:

$A_b$ = cross sectional area of the fluid bag in the plane of plate 8

$A_{ac}$ = cross sectional area of air-compressor cylinder 50

$A_{cc}$ = cross sectional area of compression cylinder 6

$D_B$ = depth in thickness of the pliant fluid bag when bag is full $V_{cc}$ = the effective volume of compression cylinder $P_{atm}$ = atmoshperic pressure $P_f$ = final absolute pressure (gauge pressure plus atmospheric pressure) that the pressure in cylinder 50 reaches, when piston head 49 is at $L_{CR}$ $P(X)$ = the pressure in the air-compressor cylinder 50 when piston head 49 is at position X R = radial arm, crank arm CFM = the flow rate of air into the compression chamber at full (predetermined) operating pressure HP = the power required for the electrical motor to develop at the end of the shaft 46

RPM = the revolutions per minute of the compressor shaft 46

T = the time, in minutes, required to empty out one bag of fluid for infusion $V_{tr}$ = transfer volume per revolution of shaft 46, the displacement volume in the compressor cylinder 50 that the compressor head 49 sweeps between the critical transfer level $L_{CR}$ and top dead center level $L_{TDC}$ TDC = top dead center level of cylinder head 49

BDC = bottom dead center level of cylinder head 49

$L_{CR}$ = *the critical level, the distance from the top of the air-compressor cylinder to the position of the cylinder head 49 in the cylinder 50 at which the orifice valve 52 opens up.*

$\Delta L = L_{CR} - L_{TDC}$

From FIG. 8 we obtain the relations:

$V_{tr} = A_{ac} \cdot L_{BDC} \cdot L_{TDC}$ $V_{cc} = A_{cc} \cdot D_B$

From the air-compressor side,

CFM = $V_{cc}$·RPM, but also from compression cylinder side

CFM = $V_{cc}$·1/T;

therefore combining these we have $$RPM = \frac{V_{cc}}{V_{tr} \cdot T} \quad (I)$$

in terms of design parameters $L_{CR}$, $L_{TDC}$, $A_{ac}$, and $D_B$

Thence we use the above cited relation $$CFM = V_{tr} \cdot RPM \quad (II)$$

In order to find the power, in units of horsepower (HP), of the electrical motor that drives the air-compressor, we need to calculate the work done by the piston head 49 per unit time in compressing air and moving the compressed air.

To calculate the power required, we use

Power = work done per revolution of shaft 46 times RPM of shaft 46  (III)

which becomes simplified if we neglect the work done by the compressed gas back on the piston head 49 on the return part of the head 49 back to the bottom dead center (BDC). Thus let $W_1$ = the work done by the compressor piston 49 in getting the pressure in the compressor cylinder 50 to the final pressure $P_f$; and $W_2$ = the work done by piston 49 in pushing the air in cylinder 50 at final pressure $P_f$ through the distance $\Delta L$ (and through the exit orifice 52 of cylinder 6); then let W = the total work done by cylinder piston 49 per advance stroke = $W_1 + W_2$.

First we calculate $W_1$ as follows $$dW_1 = P(X) A_{cc} dX$$

but from the Gas Law $$P(X) = \frac{P_{atm} \cdot L_{BDC}}{L}$$

$$= \frac{P_{atm} \cdot L_{BDC}}{L_{BDC} - X}$$

Therefore $$W_1 = \int dW_1 = P_{atm} \cdot L_{BDC} \cdot A_{ac} \cdot \int_{X=0}^{X_{cr}} \frac{dX}{L_{BDC} - X}$$

$$= A_{pist} \cdot P_{atm} \cdot L_{BDC} \cdot \ln \frac{L_{TDC} + 2R}{L_{TDC} + L}$$

A similar calculation gives $$W_2 = A_{pist} \cdot P_{atm} \cdot L_{BDC} \cdot \frac{\Delta L}{L_{TDC} + \Delta L}$$

Combining the above we obtain

Power = $(W_1 + W_2) \cdot$ RPM in terms of design parameters above.

4. Numerical Example

Let
$D_b = 2''$
$A_{ac} = 1 \text{ in}^2$
$2R = 1\frac{3}{4}''$
$\Delta L = \frac{1}{4}''$
$L_{TDC} - \frac{1}{4}''$
Therefore $L_{BDC} = 2''$ $$P_f = P_{atm} \cdot \frac{2}{0.5} = 4 \cdot P_{atm}$$

Figure 6:
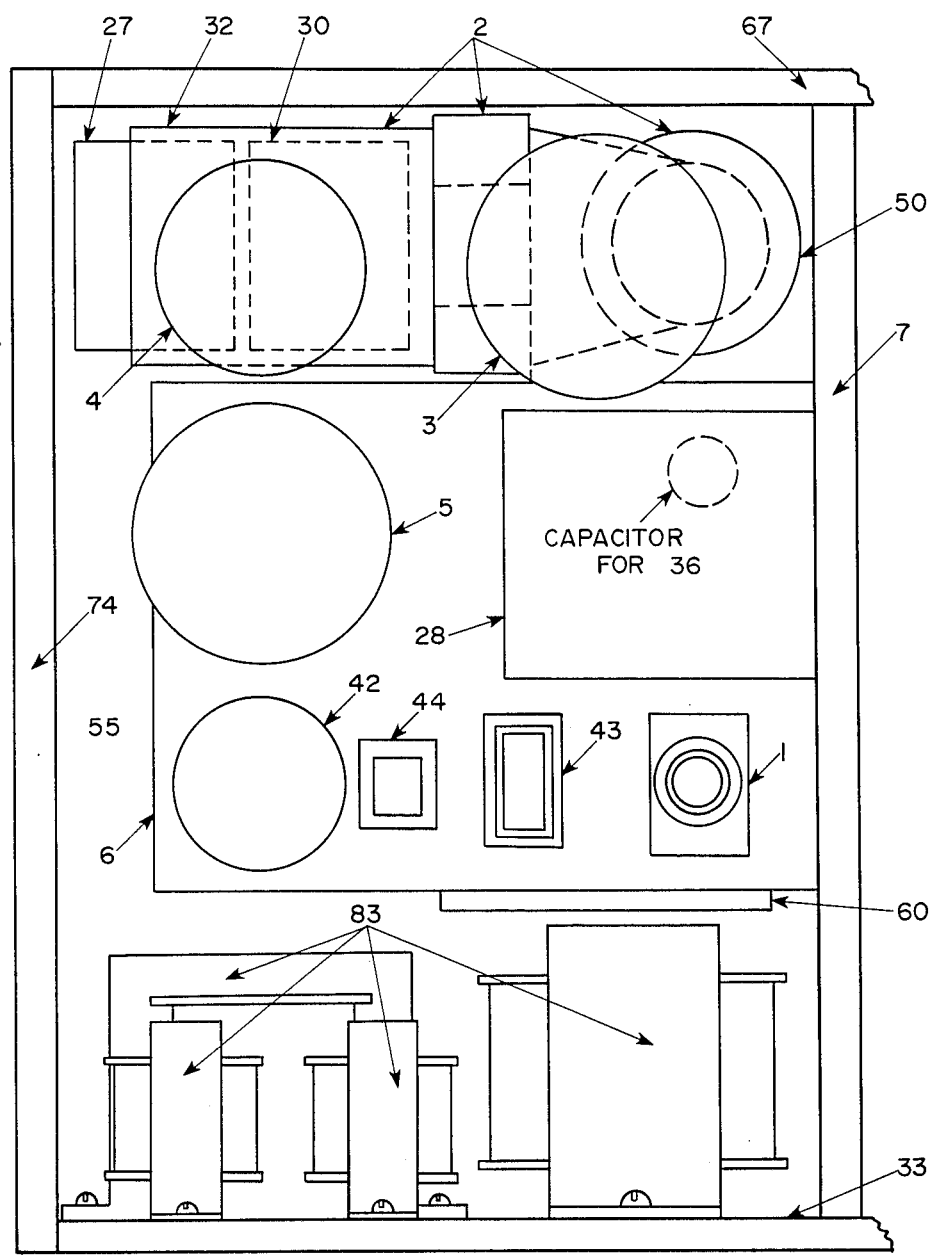
FIG. 6 shows the positions of the main components of the Automatic Infusion Device in the pressure generation-control chamber viewed from the front without the obstruction of the front panel.
Figure 7:
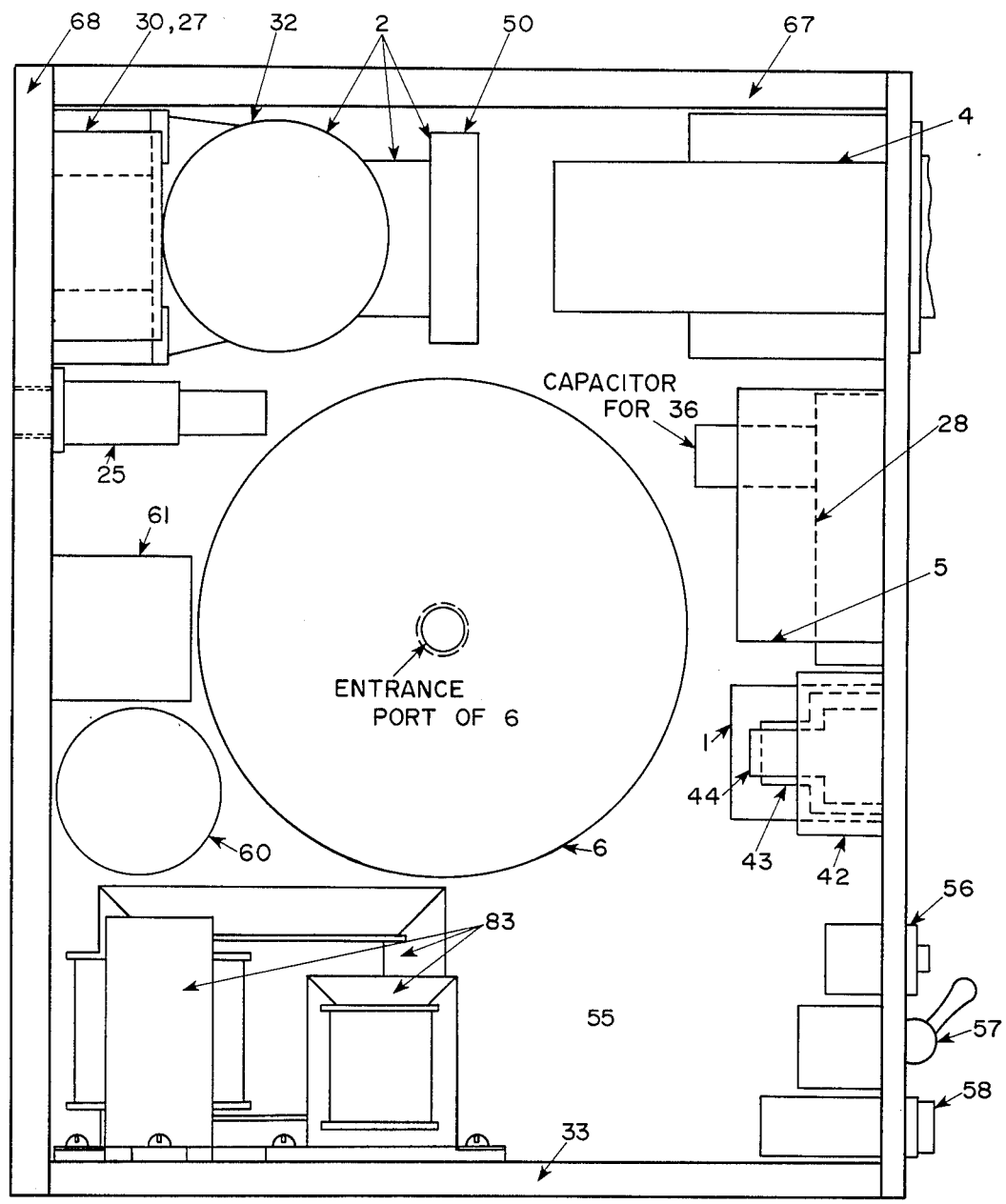
FIG. 7 shows the positions of the components of the Automatic Infusion Device shown in FIG. 6 from the left hand side of the device without obstruction from the left hand side cover plate.

The increase in pressure must be sufficient to counter the decrease of pressure due to the following design constraints for compactness of the overall device: (1) the cross section of the entire device (in the direction perpendicular to the front panel) shown in FIG. 4 should be comparable to the area $A_b$ of the fluid bag; (2) the compression cylinder 6 (which is cylindrical) has to have a sufficiently small diameter and therefore small cross section $A_{cc}$ so as to allow other components, primarily the miniature air-compressor and electronic components to have cross sections that fit in this said cross sectional area of the bag. This is illustrated in FIG. 6 and FIG. 7 explicitly. The amplification by a factor of four of the final pressure above the atmospheric pressure is indeed sufficient if we operate the fluid bag in the range of 300 and even up to 760 mm Hg (presently 300 mm Hg is the maximum allowed); thus the area reduction factor $$\frac{A_b}{A_{cc}} = \frac{(5'') \cdot (6'')}{\frac{\pi}{4} \cdot (3'')^2} \cong 4.2$$

which agrees well with the factor of 4 increase in pressure achieved by the chosen design parameters for the air-compressor.

Amplification of force is effected in the air line between the miniature air compressor 2 and pressure cylinder 6. The amplification of force corresponds to the ratio of the cross sectional area $A_{cc}$ of the piston head 15 of pressure cylinder 6 to the cross sectional area $A_{ac}$ 77 of the miniature air compressor 2.

The piston-retracting spring 22 for pressure cylinder piston 15 serves only to urge piston 15 in the direction of wall 6 after the vent port 14 of solenoid valve 4 is opened to relieve the pressure in the pressure cylinder 6 to atmospheric level. Therefore, spring 22 is weak, and just strong enough to overcome friction in the ball bushing 87 and the negligible friction of the U-packing seal 21 or a rolling diaphragm 79, which spring does not exert appreciable force during the compression part of the cycle.

Next to calculate the RPM, we need to choose the optimum desired time interval T for massive infusion of fluid. Infusion of half a liter of fluid in one minute is probably the maximum rate of flow that can be administered. Such bags have measured $D_B$ values of 2" maximum. Therefore the maximum RPM of the piston shaft is $$RPM = \frac{V_{cc}}{V_{tr} \cdot T} = \frac{7 \text{ in}^2 \cdot 2 \text{ in}}{1 \text{ in}^2 \cdot \frac{1}{4} \cdot 1 \frac{\text{min}}{\text{rev.}}}$$

Figure 11:
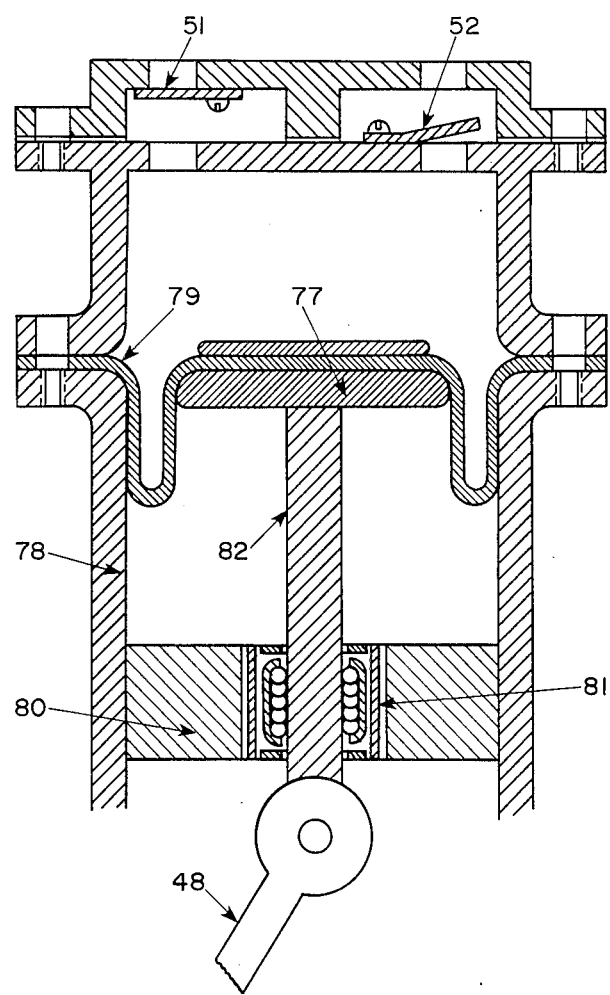
FIG. 11 shows the use of an involuted or convoluted diaphragm for the air-compressor cylinder.

= 56 revolutions per minute which is slow enough for the quiet operation of the air-compressor especially if the orifice check valves 51 and 52 are quiet and if a convoluted diaphragm design shown in FIG. 11 is incorporated between the compressor head 49 and the cylinder 50.

An infusion rate of 2 to 3 milliliters per minute is considered a normal rate of infusion as discussed in "Shafer's Medical-Surgical Nursing", 7th Edition, page 158, published by C. V. Moshy Company, St. Louis, Mo., 1980. In contrast, massive or rapid infusion rate is discussed in Anesthesiology News, Volume 10, No. 2, February, 1984, as being $2\frac{1}{4}$ liters of blood per minute. In the article by Arthur P. Vogel et al, entitled "Massive Blood Replacement" in Archives of Surgery, Volume 95, July, 1967, page 38, a rate of 500 milliliters per 15 minutes is considered massive. Therefore, the massive rate can have a range of approximately 2 liters per minute to 500 milliliters per 15 minutes, a rate of 1 liter per minute being a reasonable massive rate for which the above calculations have been made.

To calculate the HP we first calculate $W_1$ and $W_2$ for the chosen design parameter values $$W_1 = 1''^2 \cdot 14.7 \text{ psi} \cdot 2'' \cdot \ln\left(\frac{\frac{1}{4} + 1\frac{3}{4}}{\frac{1}{4} + \frac{1}{4}}\right) \cdot \frac{1 \text{ ft.}}{12 \text{ in.}}$$

= 3.5 ft-pound/cycle $W_2 = W_1 \cdot (0.5/1.42) = 1.23$ ft-lb/cycle $W = 4.7$ ft-lb/cycle Combining with the RPM calculated, we obtain the power P in horse-power units:

$$P = 4.7 \text{ ft-lb/cycle} \cdot 56 \text{ cycles/min} \cdot \frac{1 \text{ H.P.}}{33,000 \frac{\text{ft-lb}}{\text{min.}}}$$

$= 8 \times 10^{-3}$ H.P.

$\cong \frac{1}{100}$ H.P.

which means that the electric motor can be rather small, on the order of or less than one and a half inches in diameter and about two inches long. Thus a miniature low noise-air compressor can be designed with sufficient power for massive fluid infusion.

SPECIFIC EMBODIMENTS

That the infusion device hereby disclosed can be so designed as to make it compact, portable and operable in a number of different operational settings such as emergency vehicle, field, emergency room, patient bedside in addition to the operating room, is a claim of this disclosure that is substantiated by the specific design details given in this subsection.

Figure 5:
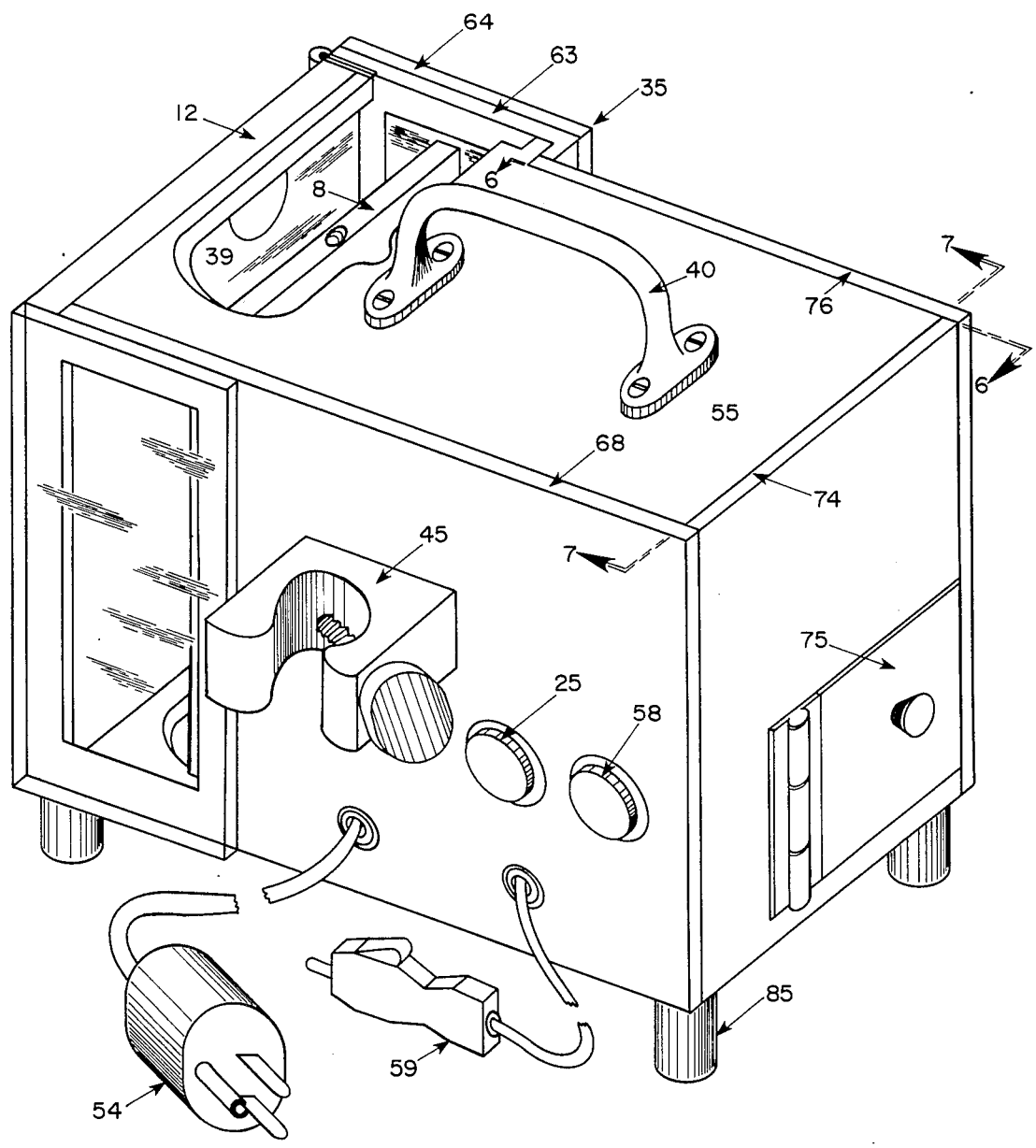
FIG. 5 is a perspective from the back and left hand side of the device showing how it is to be clamped to poles and power input cords as well as an optional hand bulb-tube location.
Figure 9:
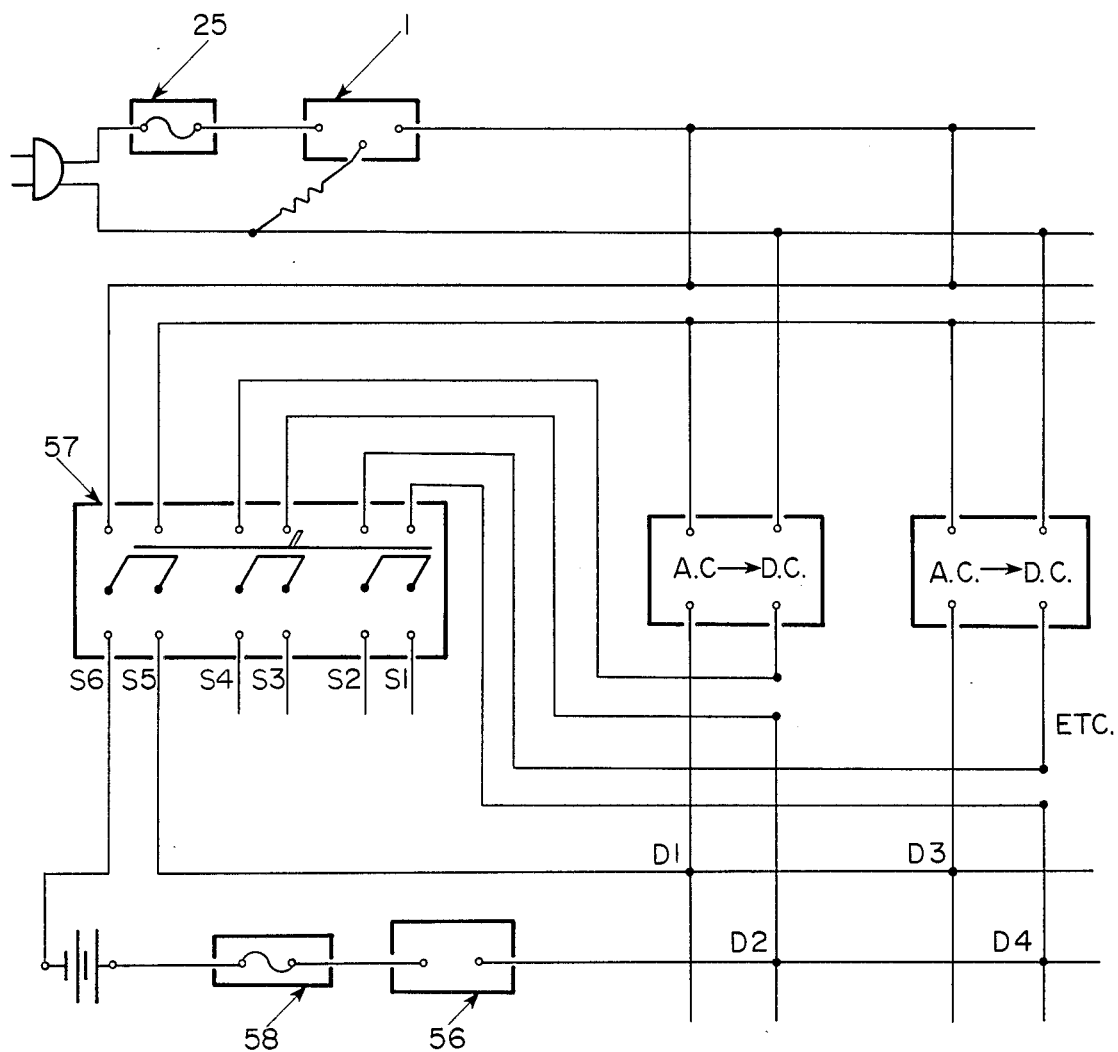
FIG. 9 is a diagram showing how to modify the circuitry in FIG. 3 so as to be able to operate the Automatic Infusion Device in A.C. or D.C. mode by switching from one to the other with a toggle switch.

FIG. 9 shows the changes in the electrical circuitry to achieve both A.C. and D.C. operation in one embodiment; furthermore, FIG. 7 shows that there is sufficient space left, in the said depicted embodiment, at the lower front section of the pressure generation-control chamber 55. There is sufficient space left also in the front panel 76 (see FIG. 2) of this empty section to accommodate a D.C. switch 56, and A.C.-D.C. toggle switch 57 for A.C. or D.C. mode selection, and a D.C. fuse 58 which can be alternatively positioned near the A.C. fuse mounted on the back plate as shown in FIG. 5. A D.C. plug 59 such as that for an auto cigarette lighter is to be used in the D.C. mode and its position is shown in FIG. 5. In the embodiment depicted in FIG. 2, pressure regulation is accomplished by adjusting knob 19 of mechanical pressure regulator 3; however, said pressure regulation (over a wide range) that provides normal to massive infusion, can also be accomplished by means of electrical-electronic control of the speed of the air-compressor motor 32 in place of or in addition to the said mechanical pressure regulation means.

Even with these additional components there is sufficient space left for a large capacitor 60 and a large rectifier giode 61 for the A.C. D.C. converter 31 of the air-compressor motor 32 in the back part of the pressure generation-control chamber as shown in FIG. 7. Also the First Relay 27 and the Second Relay 30 fit well between the said motor 32 and the back plate 68. The few remaining electronic components are sufficiently small to be mounted in a variety of convenient locations. The present disclosure, the Automatic Infusion Device, is thus well suited for applications in emergency vehicles particularly also because of the high current capacity of the vehicle batteries and the small size yet high current D.C. motors that can be used to run the miniature air compressor 2. The particular modification that need to be made in the circuitry to accommodate D.C. operation are shown in FIG. 9 where the junctions D1, D2, etc. are shown that are also identified in FIG. 3. If only D.C. operation is desired, the branches before these junctions are to be eliminated.

Figure 10:
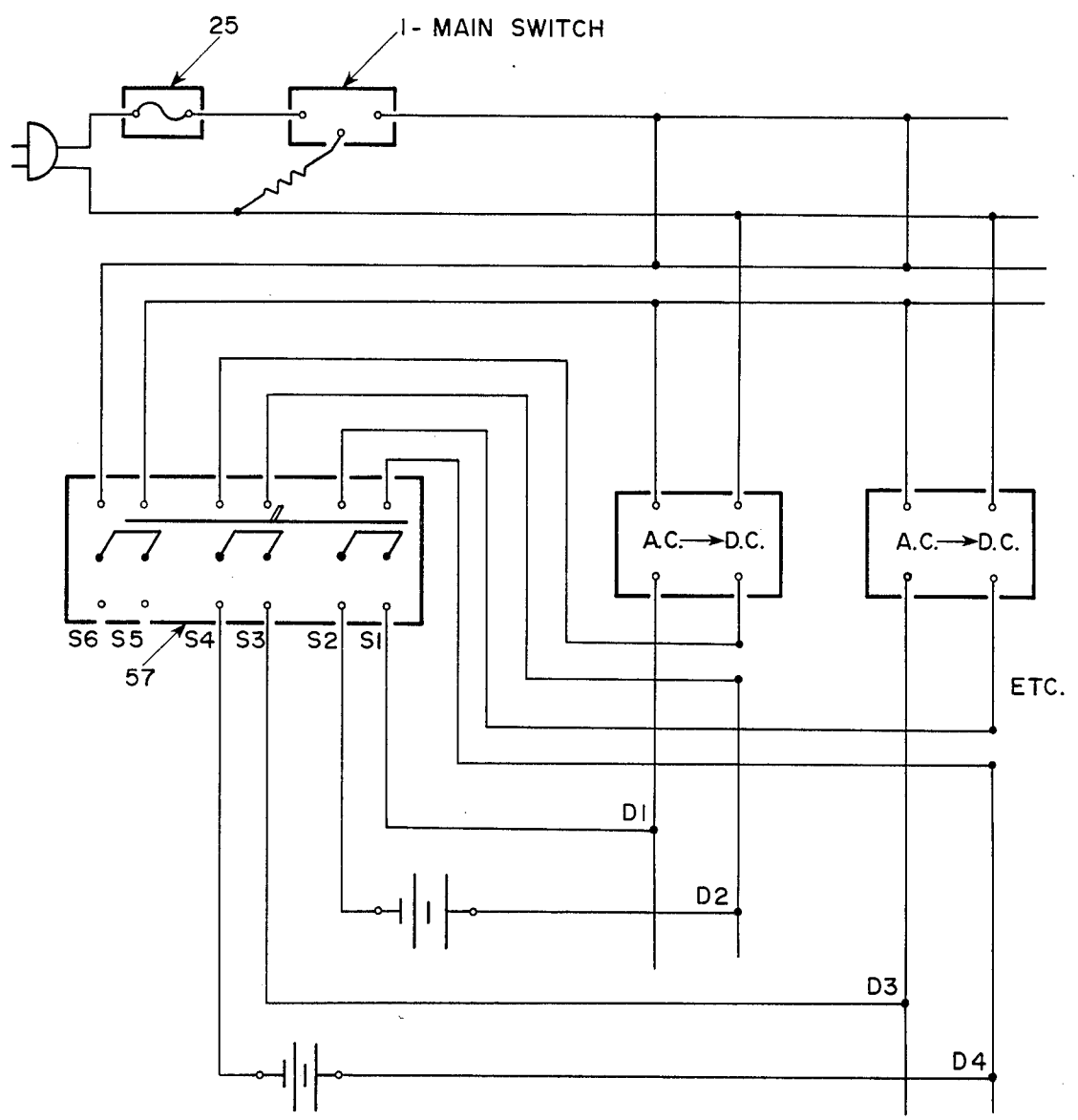
FIG. 10 shows modifications to be made to the circuitry of FIG. 3 in order to have an embodiment that is operable on batteries.

Another embodiment of the D.C. mode is to use rechargeable batteries; however in this case it is advantageous to power the latching circuit 28 separately from the air-compressor motor 32 and even these separately from the three-way solenoidal valve circuit; for this purpose a "multipole" switch diagrammatically depicted in FIG. 10 can be used. This mode allows the operation of the Automatic Infusion Device temporarily away from A.C. or D.C. power sources such as in parts of a hospital.

Figure 13:
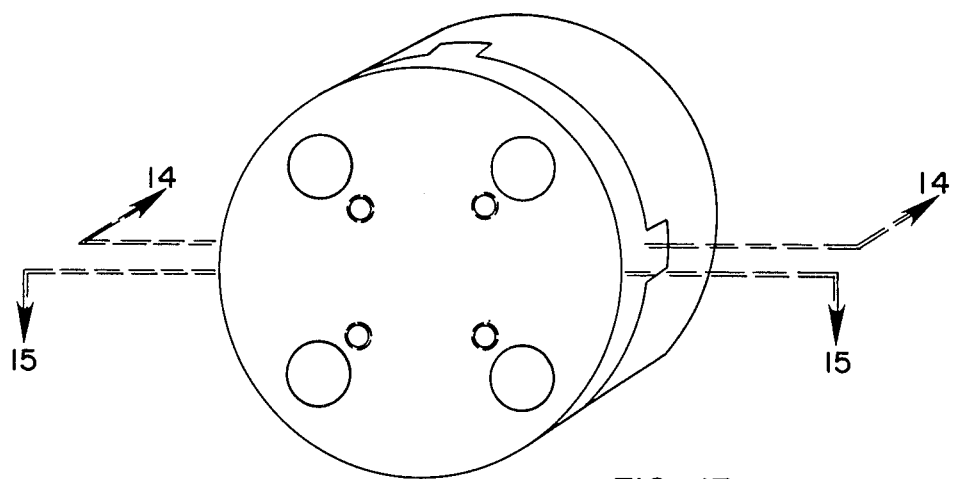
FIG. 13 shows a perspective drawing of a cylindrical adaptor for pole clamps to make the Automatic Infusion Device usable with horizontal or vertical poles as desired.
Figure 14:
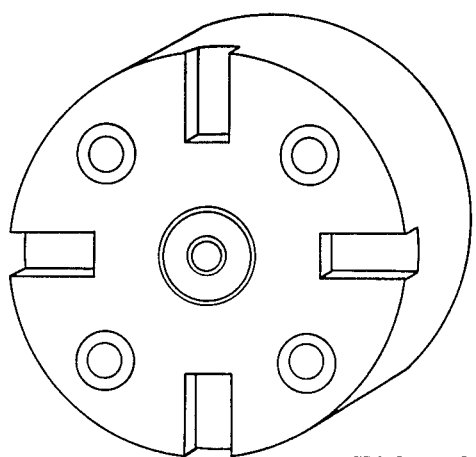
FIG. 14 shows the female component of the rotatable clamp adaptor shown in FIG. 13.
Figure 15:
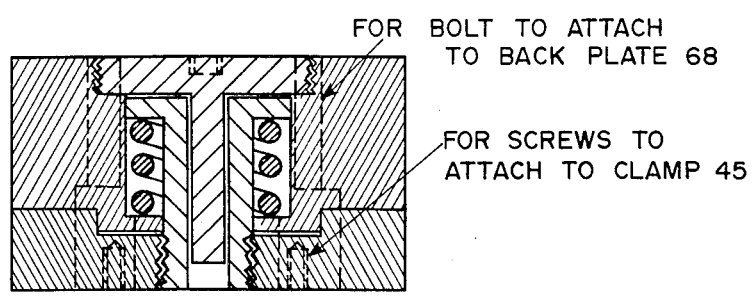
FIG. 15 shows a cross sectional view of the adaptor shown in FIG. 13.

In all the above cases the use of a clamp 45 shown in FIG. 5 in conjunction with a "rotatable clamp adaptor" depicted in FIG. 13, FIG. 14 and FIG. 15 allows the Automatic Infusion Device to be clamped to a vertical or a horizontal pole or rod such as vertical or horizontal parts of the railings to the beds of patients or to such poles in the operating rooms.

FIG. 2 shows the actual embodiment of the total device in a frontal perspective. FIG. 2, FIG. 6 and FIG. 7 together show that the device, in this embodiment, has approximate dimensions of: width 8.5", height 7¾, depth 6" not including the clamp 60, the handle 40, footings 85 and protrusions such as knobs and the toggle switch. The device is therefore compact and mountable on any and such poles that hold blood warmers with which the Automatic Infusion Device would be associated. This combination is operationally desirable as it improves the effectiveness of the infusion process.

The transparent door 35, the transparent stationary vertical end plate 12 shown in FIG. 2 and the transparent opening of back plate 68 in the compression chamber section (shown in FIG. 5) allow clear visibility of the bag during the whole cycle of operation and held in the placement and removal of said bag into the compression chamber.

FIG. 2 shows details of the bag compression chamber door 35 made up of a frame 63 which can bear loads and latches over the protrusion of central vertical plate 7 and is attached to the right hand side end plate 12 with a piano hinge that can bear loads. The said door has a transparent overlay 64. A simple magnetic latch 65 or an equivalent and a knob 66 are also shown in FIG. 2.

A design of the compression chamber that would eliminate the need for bracket-like feature of the top plate 67 and bottom plate 33 would be alternative designs of door 35 as follows: either a one-piece right-angled door or a single flat door hinged on either the left or the right hand sides or on top or bottom plates with corresponding positions for the locking mechanism.

The design of the compression chamber 55 can be simplified if one is willing to use a single molded transparent piece that approximately envelopes that full bag in its hung position thus replacing the door 62, end plate 12 and part of the back plate 68 in the compression chamber 39. Also the particular embodiment shown in FIG. 2 can be operated without the door 62 as a load bearing member or with no door at all due to the special design of the top plate 67 (see also FIG. 4) and the bottom plate 33 which, while they have cut-outs in the compression chamber section, nevertheless they do allow pressure to be applied to plate 12 without distortion of said plate 12 due to the bracket-like form of these cut-outs that hold plate 12 in place. The top plate 67 and bottom plate 33 are thus to be made of high strength material. Top plate 67 also will bear the load of the Automatic Infusion Device via handle 40 that is attached to it. Brackets 70 further assist in strengthening the transparent end plate 12.

The separation of the pressure generation-control chamber 55 from the compression chamber 39 has the further advantage that said compression chamber can be made autoclavable together with the door 35, the pressure plate 8 and cylinder rod 17 because the said compression chamber can be so attached to the central plate 7 as to be detachable from said plate 7; this is accomplished, for example, in a design of the chamber that makes use of pressure bearing hinges or tongue and groove to attach the chamber to the plate 7; first the part of the chamber that envelopes the bag would be removed and then the push plate 8 and rod 17 would be unscrewed to get these parts autoclaved; also electrical connectors could be so designed as to make switches 20 and 26 detachable.

By maintaining the essential integrity of the pressure-generation-control chamber but with minor modifications in design, such as possible elimination of the pressure cylinder and the addition of pliant (and possibly elastic) membranes to replace the piston compression plate 8 and possibly also the bag enveloping portion of the compression chamber, an embodiment of the device results which could also be used as an automatic means of pressure application. Also minimally a simpler combination of the components of the pressure-generation and control portion of the presently disclosed device could be used for all said purposes, a combination such as the miniature air-compressor, a pressure regulator and parts of the electronic control so as not to be dependent upon sources of already pressurized gas.

The flatness of the bottom plate 33 and the box design allow the use of the device on horizontal surfaces such as tables. In addition, footings of various lengths, such as the footings 85 shown in FIG. 2 and FIG. 5 can be added to the said device to allow tubings attached to exit port 18 of the fluid bag 9, as well as other attachments to the fluid bag such as blood filters, to protrude freely between bottom plate 33 and the top of the platform or table on which the Automatic Infusion Device stands with its said footings. The said footings can be permanent or removable, foldable or retractable into the housing chambers.

The Automatic Infusion Device will have two hooks, one for horizontal position shown in FIG. 4 with a strap 11 and a vertical one with an alternate tapping hole shown on plate 8 in FIG. 4. While the vertical one can protrude above top plate 67, the horizontal one needs a hole 72 on plate 12 shown in FIG. 2 and FIG. 4. An additional hole 73 is provided in plate 12 to allow nipples of bags (that are used for adding medication to the fluid of the bag while said bags are in use) to protrude freely through plate 12. Said hole 73 can be tapped so that it can be closed with a removable threaded plug for bags that do not have an injection site nipple.

The handle 40 of the device is so positioned as to have the weight of the device balanced with respect to it when lifted. The heavier components such as the compression cylinder, transformers, the air-compressor are distributed in as much as practicable in such a way as to distribute these weights almost evenly but somewhat toward the back part nearer to clamp or clamps 45. The circuits shown in FIG. 3 and FIG. 9 are so designed as to make hand bulb operation (with its own vent) feasible whenever power failure occurs or when hand bulb mode of operation is chosen by the operator (using toggle switch 57). In this mode the three-way solenoidal valve vent port 14 communicates directly with the pressure cylinder also closing off port 24 to the air-compressor.

FIG. 11 shows details of another embodiment of the air-compressor compression chamber shown in FIG. 8. The air-compressor 2 can be so designed as to have zero leakage between piston head 77 and cylinder wall 78 of FIG. 11 thereby allowing the compressor to generate higher pressures for a given power level of the electric motor of the said air-compressor; this is accomplished using involuted or convoluted diaphragms 79 shown, for example, in FIG. 11, assuming also that good check valves or equivalents (diagramatically shown as parts 51 and 52) are used. However in this case an additional collar 80 with ball bushing 81 is needed to keep piston rod 82 and piston head aligned parallel to the cylinder wall 78 at all times.

If the RPM of the electric motor is too high as compared to the value given by the quantitative analysis presented above, then reduction gears need to be used between the motor shaft and shaft 46 (shown in FIG. 8) of the air-compressor. Note that FIG. 8 depicts components of air-compressor 2 not in the same scale as that of the pressure cylinder 6 also depicted therein. The translation arm 48 of the compressor 2 should be made of such dimension as to avoid interference with cylinder wall 78; this and the addition of collar 80 can make the dimension of the compressor 2 in the direction of the cylinder (perpendicular to motor shaft and shaft 46 direction) too long for vertical positioning of the complete air-compressor in the pressure generation-control chamber, assuming that we adhere to dimensions already chosen and assuming that the pressure cylinder 6 is centrally located on plate 7; however because there is sufficient empty space left in the lower part of this said chamber, the air-compressor 2 can be positioned horizontally in the lower part of this chamber by rearranging the transformers 83 (shown in FIG. 6 and FIG. 7) in same said section of the chamber. An optional additional fuse 69 can be used for the electric motor of the air-compressor also in this section of the said chamber.

Figure 12:
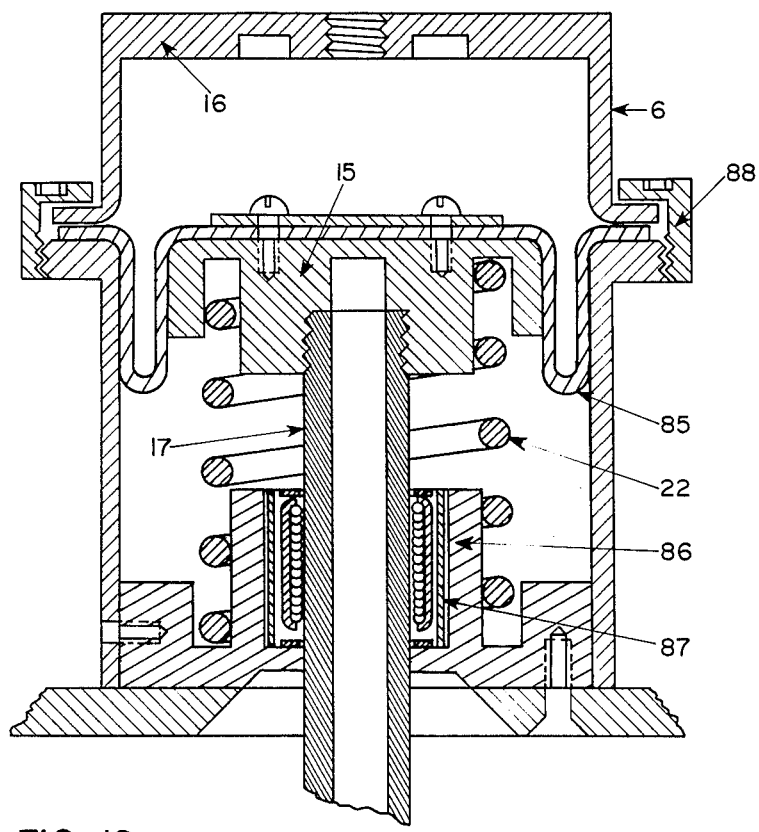
FIG. 12 shows the use of an involuted or convoluted diaphragm, in place of a U-seal, for the compression cylinder shown in FIG. 4.

FIG. 12 shows the pressure cylinder 6 similar to that of FIG. 2 but replacing the U-packing seal 21 with diaphragm 85. Again a collar 86 ensures alignment of the piston parallel to cylinder wall. A ring type locking collar 88 ensures easy access to cylinder head and diaphragm and provides flexibility to align plate 8 vertically after piston rod 17 is attached to collar 62 attached to compression plate 8.

The use of the diaphragm instead of an O-ring or a U-seal reduces friction between cylinder head and cylinder wall so that a spring with a smaller spring constant can be used, the spring chosen just stiff enough to push out the compressed air when vent 14 is opened to the atmosphere and cause the piston to retract.

The convoluted diaphragm design provides high reliability particularly since very few strokes per minute are to be executed and the duty cycle of the Automatic Infusion Device is rather low compared to most industrial applications for automation-even when rapid sequantial infusion is called for. Furthermore the high-current miniature D.C. motors that are available on the market are also very reliable at these duty cycles. Even so, an additional optional hand-bulb squeeze mode of operation of the device as well as use of gas from cylinders and outlets provides an added precautionary measure; the device has sufficient empty space to accommodate such additional components and FIG. 5 shows chamber 75 designated for the addition of such components.

The versatility of the device achieved due to the specific design features discussed above in connection with various embodiments will allow its use in a large number of operational conditions including field use, upper atmosphere, space and outer space applications and field use that include high stress situations. For applications where there is no air or not sufficient air in the environment, a reservoir of gas can be used in a hermetically sealed embodiment; the compression cylinder 6 is then replaced with a double acting one with flow switches that allow either side of the piston head 15 to be acted upon by the high or low pressure parts of the sealed system as in usual practice.

The uses of the presently disclosed device are not limited to parenteral ones; an example of other uses is irrigation with pressurized solutions for aiding surgery.

The device size is small enough to allow a slight increase in its dimensions to admit sound insulation for extremely quiet operation even beyond the considerations given in the subsection above on quantitative analysis that showed that quiet operation was achievable with small number of piston strokes of the air-compressor. Beyond this, metallic shielding can be provided for all electronic components to insure that no induced electrical interferences will occur to apparata outside the present apparatus or to itself from outside sources.

The components in the pressure generation and control chamber are so assembled as to allow easy disassembling of the device and easy access to its components; thus the components on front panel 76 and back plate 68 are so mounted as to move said plates with components and wiring intact pivoting them around the lower front and back edges respectively of the base plate.

What is claimed is:

1. Portable apparatus for infusing a fluid from a pliant fluid container having an exit port, through a tubular member into a human body at rates of normal to massive infusion, including
   (a) a boxlike member having fixed top, bottom, side and end walls
   (b) a rigid movable pressure plate within said boxlike member extending between the side walls thereof, and normally lying in spaced relation to the end walls, thereby forming a compression chamber between said movable wall and one of said fluid end walls
   (c) a support member carried by said movable plate on the compression chamber side thereof, for holding the pliant fluid container in engagement with said pressure plate
   (d) a door in one of the sides of said boxlike member providing access to the compression chamber, for inserting a filled, pliant fluid container into the compression chamber, and removing empty pliant fluid containers therefrom
   (e) a piston and cylinder mounted in said boxlike member, one end of said piston being engaged with said pressure plate for moving the latter through the compression chamber and squeezing the pliant fluid container between the pressure plate and said one end wall to discharge the fluid in the fluid container through the exit port thereof
   (f) air pressure means operatively engaged with said piston and cylinder for actuating the former to maintain a constant pressure on the fluid container to discharge the entire contents thereof
   (g) a pressure regulator connected to said air pressure means to selectively vary the range of discharge of fluid from the pliant fluid container.
   (h) power means in circuit with said air compressor for activating the latter
   (i) switch means in circuit with said air compressor for halting the movement of said pressure plate after the pliant fluid bag has be emptied, and
   (j) spring means for retracting said piston and pressure plate upon actuation of said switch means
   (k) said pressure plate engaging an end wall of said boxlike member after it has been retracted to its initial position.

2. Portable apparatus for infusing a fluid from a pliant fluid container having an axis port, through a tubular member into a human body at rates of normal to massive infusion, including
   (a) a boxlike member having fixed top, bottom, side and end walls
   (b) a rigid movable wall within this boxlike member extending between the side walls thereof and normally lying in spaced relation to the end walls, thereby forming a compression chamber between said movable wall and one of said fixed end walls
   (c) a support member carried by said movable wall in the compression chamber side thereof, for holding the pliant fluid container in engagement with said movable wall
   (d) a door in one of the side walls of said boxlike member providing access to said compression chamber, for inserting a filled pliant fluid container into the compression chamber, and removing the empty pliant fluid container therefrom
   (e) a pressure cylinder having a piston rod and piston head connected to one end of the piston rod mounted in said boxlike member, the free end of said piston rod being engaged with said movable wall, for moving the latter through the compression chamber and squeezing the pliant fluid containing between the movable wall an said one end wall to discharge the fluid through the exit port thereof
   (f) an air compressor
   (g) power means for actuating said air compressor
   (h) an air line connecting said air compressor to said cylinder, whereby a continuous pressure is exerted on the pliant fluid container's
   (i) pressure regulating means in said air line between the air compressor and cylinder to selectively vary the rate of discharge of fluid from the pliant fluid container
   (j) a normally open electrical switch in circuit with said power means and air compressor mounted on the compression chamber side of said movable wall, said electrical switch engaging said one fixed end wall upon depletion of the fluid in the pliant bag to close the switch, whereby said power means and air compressor are deactivated, and
   (k) a convolute spring mounted on said piston rod between said piston head and said fixed end walls of the boxlike member for automatically reversing the direction of movement of said movable wall upon closing of said electrical switch, and retracting the piston rod, piston head and movable wall to their original position, at which time the empty fluid container is removed.

3. The portable apparatus of claim 2, wherein
   (a) said pressure regulating means includes a pressure regulator
   (b) a solenoid valve in said air line between said air compressor and cylinder
   (c) said solenoid valve including extrance and axis air vent ports
   (d) electronic control means in circuit with said solenoid valve for allowing pressurized air from the pressure regulator to pass through the entrance air vent port of said solenoid valve to said cylinder, and to close the entrance port thereof during operation of the apparatus
   (e) said electronic control means being triggered by the closing of said electrical switch to channel air through the exit air vent port of said solenoid valve and close the entrance air vent port thereof, thereby enabling said piston rod, piston and movable wall to retract under urging of said convolute spring.

4. Portable apparatus for infusing a fluid from a pliant fluid container having an exit port, through a tubular member into a human body, including
   (a) a boxlike member having fixed top, bottom, side and end walls
   (b) a rigid movable wall within said boxlike member extending between the side walls thereof, and normally lying in spaced relation to the end walls thereby forming a compression chamber between said movable wall and one of said fixed end walls
   (c) a support member carried by said movable wall on the compression chamber side thereof, for holding the pliant fluid container in engagement with said movable wall
   (d) a first means in said boxlike member providing access to said compression chamber for inserting a filled fluid container into the compression chamber, and removing empty pliant fluid containers therefrom (e) a second means comprising a piston and cylinder, mounted in said boxlike member, one end of which piston is engaged with said movable wall, for moving the latter through the compression chamber and squeezing the pliant fluid container between the movable wall and said one end wall, to discharge the fluid in the fluid container through the exit port thereof and the tubular member into the body (f) a third means operatively engaged with said piston for maintaining a continuous pressure on the pliant fluid container for discharging the contents thereof (g) said third mans comprising an air compressor (h) an air line connecting said air compressor to said cylinder for transmitting compressed air (i) a fourth means for regulating said air compressor to selectively vary the rate of discharge of fluid from the pliant fluid container (j) said fourth means comprising a pressure regulator in said air line between the air compressor and cylinder (k) a fifth means for automatically reversing the direction of movement of said movable wall after the fluid container has been emptied (l) a sixth means for halting movement of the movable wall after it has been retracted to its initial position (m) power means in circuit with said third means for actuating the same, and (n) a solenoid valve in said air line and in circuit with said power means for controlling the flow of air to said cylinder.

5. The portable apparatus of claim 4, with the addition of (a) an eighth means for amplifying the force exterted by the compressed air on the piston of said second means to a degree that fluid may be expelled from the pliant fluid container at a massive rate (b) said fourth means selectively controlling the pressure of the compressed air delivered by the air compressor to the compression member for varying the rate of discharge of fluid from the fluid container at rates of normal to massive infusion.

6. The portable apparatus of claim 5, wherein (a) said air compressor includes a piston (b) the cross sectional area of the piston of said second means being substantially greater than the cross sectional area of the piston of said air compressor, to amplify the force exerted by the piston of said air compressor on the compressed air, said amplification force being in the ratio of the cross sectional area of the piston of said second means to the cross sectional area of the piston of the air compressor.

7. The portable apparatus of claim 6, wherein (a) said movable wall is flat and substantially coextensive in height and width with the pliant fluid container.

8. Portable apparatus for pumping a fluid from a pliant fluid container having an exit port through a tubular member into a human body, including (a) a boxlike member having fixed top, bottom, side and end walls (b) a rigid movable wall within said boxlike member extending between the side walls thereof, and normally lying in spaced relation to the end walls, thereby forming a compression chamber between said movable wall and one of said fixed end walls (c) a support member carried by said movable wall in the compression chamber side thereof, for holding the pliant fluid container in engagement with said movable wall (d) a first means in said boxlike member providing access to said compression chamber for inserting a filled fluid container into the compression chamber, and removing empty fluid containers therefrom (e) a second means comprising a piston and cylinder, mounted in said boxlike member, one end of which piston is engaged with said movable wall, for moving the latter through the compression chamber and squeezing the pliant fluid container between the movable wall and said one end wall, to discharge the fluid in the fluid container through the exit port thereof (f) a third means operatively engaged with said piston for maintaining a continuous pressure on the pliant fluid container discharging the contents thereof (g) a fourth means for regulating said third means to selectively vary the rate of discharge of fluid from the pliant fluid container (h) a fifth means for automatically reversing the direction of movement of said movable wall after the fluid container has been emptied (i) said fifth means comprising an electrical switch in circuit with said power means and said third means, for cutting off the former (j) spring means engages with said piston for urging the latter to a retracted position (k) a sixth means for halting movement of the movable wall after it has been retracted to its initial position, and (l) power means in circuit with said third means for actuating the same.

9. Portable apparatus for pumping a fluid from a pliant fluid container having an exit port through a tubular member into a human body, including (a) a boxlike member having fixed top, bottom, side and end walls (b) a rigid movable wall within said boxlike member extending between the side walls thereof, and normally lying in spaced relation to the end walls, thereby forming a compression chamber between said movable wall and one of said fixed end walls (c) a support member carried by said movable wall in the compression chamber side thereof, for holding the pliant fluid container in engagement with said movable wall (d) a first means in said boxlike member providing access to said compression chamber for inserting a filled fluid container into the compression chamber, and removing empty fluid containers therefrom (e) a second means comprising a piston and cylinder, mounted in said boxlike member, one end of which piston is engaged with said movable wall, for moving the latter through the compression chamber and squeezing the pliant fluid container between the movable wall and said one end wall, to discharge the fluid in the fluid container through the exit port thereof (f) a third means operatively engaged with said piston for maintaining a continuous pressure on the pliant fluid container discharging the contents thereof (g) a fourth means for regulating said third means to selectively vary the rate of discharge of fluid from the pliant fluid container (h) a fifth means for automatically reversing the direction of movement of said movable wall after the fluid container has been emptied, and (i) a sixth means comprising a fixed end wall of said boxlike member engaged by said movable wall for halting movement thereof.

10. Portable apparatus for pumping a fluid from a pliant fluid container having an exit port, through a tubular member into a human body, including (a) a boxlike member having fixed top, bottom, side and end walls (b) a rigid movable wall within said boxlike member extending between the side walls thereof, and normally lying in spaced relation to the end walls, thereby forming a compression chamber between said movable wall and one of said fixed end walls (c) a first means for holding the pliant fluid container in engagement with said movable wall within the compression chamber (d) a compression member comprising a piston and cylinder mounted in said boxlike member, one end of which piston is engaged with said movable wall, for moving the latter through the compression chamber and squeezing the pliant fluid container between the movable wall and said one end wall, to discharge the fluid in the container through the exit port and tubular member into the human body (e) an air compressor including a piston and cylinder (f) an air line for delivering compressed air from said air compressor to said compression member (g) power means for actuating said air compressor to deliver compressed air to said compression member to effect movement of said movable wall into squeezing engagement with the pliant fluid container (h) a second means for amplifying the force exerted by said air compressor through the compression member on the movable wall to a degree that fluid may be expelled from the pliant fluid container at a massive rate, and (i) pressure regulating means in said air line to selectively control the pressure of the compressed air delivered by the air compressor to the compression member for varying the rate of discharge of fluid from the pliant fluid container at rates of normal to massive infusion.

11. The portable apparatus of claim 10 wherein (a) the cross sectional area of the compression member piston is substantially larger than the cross sectional area of the air compressor piston to amplify the force exerted by the piston of said air compressor on the compressed air, said amplification force being in the ratio of the cross sectional area of the piston of the compression member to the cross sectional area of the piston of the air compressor (b) said amplified force being transmitted by said compression member piston to said movable wall for expelling fluid from the fluid container at a massive rate when said regulating means are adjusted to permit application of the maximum force to the pliant fluid container.

12. The portable apparatus of claim 11, wherein (a) said movable wall is flat and substantially coextensive in height and width with the pliant fluid container.

13. The portable apparatus of claim 11, with the addition of (a) a third means for automatically reversing the direction of movement of said movable wall after the fluid container has been emptied, and (b) a fourth means for halting movement of the movable wall after it has been retracted to its intial position.

* * * * *